(12) United States Patent
Nichols et al.

(10) Patent No.: US 10,709,478 B2
(45) Date of Patent: Jul. 14, 2020

(54) ORTHOPEDIC FIXATION DEVICES AND METHODS OF INSTALLATION THEREOF

(71) Applicant: GLOBUS MEDICAL, INC., Audubon, PA (US)

(72) Inventors: Jeff Nichols, Philadelphia, PA (US); Noah Hansell, King of Prussia, PA (US)

(73) Assignee: Globus Medical, Inc., Audobon, PA (US)

( * ) Notice: Subject to any disclaimer, the term of this patent is extended or adjusted under 35 U.S.C. 154(b) by 232 days.

(21) Appl. No.: 15/987,155

(22) Filed: May 23, 2018

(65) Prior Publication Data

US 2018/0263664 A1    Sep. 20, 2018

Related U.S. Application Data

(60) Continuation of application No. 15/409,600, filed on Jan. 19, 2017, now Pat. No. 9,999,447, which is a continuation-in-part of application No. 15/193,289, filed on Jun. 27, 2016, now Pat. No. 9,681,894, which is a continuation-in-part of application No. 14/514,796, filed on Oct. 15, 2014, now Pat. No. 9,549,763, which is a division of application No. 13/183,965, filed on Jul. 15, 2011, now Pat. No. 8,888,827.

(51) Int. Cl.
| | | |
|---|---|---|
| *A61B 17/04* | (2006.01) | |
| *A61B 17/86* | (2006.01) | |
| *A61F 2/08* | (2006.01) | |
| *A61B 17/70* | (2006.01) | |
| *A61B 17/88* | (2006.01) | |
| *A61B 17/56* | (2006.01) | |
| *A61B 17/68* | (2006.01) | |

(52) U.S. Cl.
CPC ...... *A61B 17/7032* (2013.01); *A61B 17/7035* (2013.01); *A61B 17/7037* (2013.01); *A61B 17/7049* (2013.01); *A61B 17/7056* (2013.01); *A61B 17/7082* (2013.01); *A61B 17/8605* (2013.01); *A61B 17/8685* (2013.01); *A61B 17/888* (2013.01); *A61B 2017/567* (2013.01); *A61B 2017/681* (2013.01)

(58) Field of Classification Search
CPC combination set(s) only.
See application file for complete search history.

(56) References Cited

U.S. PATENT DOCUMENTS

| | | |
|---|---|---|
| 5,716,356 A | 2/1998 | Biedermann et al. |
| 6,280,442 B1 | 8/2001 | Barker et al. |
| (Continued) | | |

FOREIGN PATENT DOCUMENTS

| | | |
|---|---|---|
| DE | 9314297 U1 | 5/1994 |
| EP | 1459690 A1 | 9/2004 |
| FR | 2720262 A1 | 12/1995 |

*Primary Examiner* — Sameh R Boles

(57) ABSTRACT

Orthopedic fixation devices and methods of installing the same. The orthopedic fixation device may include a coupling element and a bone fastener, whereby the bone fastener can be loaded into the coupling element through the bottom of a bore in the coupling element and a retention member is configured to allow polyaxial rotation of the bone fastener and also to lock the bone fastener in place upon application of a force on a saddle and clamp in the coupling element.

20 Claims, 34 Drawing Sheets

(56) References Cited

U.S. PATENT DOCUMENTS

| | | |
|---|---|---|
| 6,485,491 B1 | 11/2002 | Farris et al. |
| 6,660,004 B2 | 12/2003 | Barker et al. |
| 6,695,846 B2 | 2/2004 | Richelsoph et al. |
| 7,678,136 B2 | 3/2010 | Doubler et al. |
| 7,727,261 B2 | 6/2010 | Barker et al. |
| 8,100,948 B2 | 1/2012 | Ensign et al. |
| 8,133,262 B2 | 3/2012 | Whipple |
| 8,221,457 B2 | 7/2012 | Delecrin et al. |
| 8,298,274 B2 | 10/2012 | Barker, Jr. et al. |
| 8,435,266 B2 | 5/2013 | Richelsoph |
| 8,657,857 B2 | 2/2014 | Dall et al. |
| 8,685,064 B2 | 4/2014 | Hestad et al. |
| 8,979,898 B2 | 3/2015 | Ark et al. |
| 8,998,960 B2 | 4/2015 | Jackson |
| 9,055,980 B2 | 6/2015 | Biedermann |
| 9,168,069 B2 | 10/2015 | Jackson et al. |
| 9,333,016 B2 | 5/2016 | Biedermann et al. |
| 9,504,497 B2 | 11/2016 | Ark et al. |
| 9,522,021 B2 | 12/2016 | Jackson et al. |
| 9,615,867 B2 | 4/2017 | Picetti et al. |
| 9,820,780 B2 | 11/2017 | Duncan et al. |
| 2002/0035366 A1 | 3/2002 | Walder et al. |
| 2004/0267264 A1 | 12/2004 | Konieczynski et al. |
| 2005/0171537 A1 | 8/2005 | Mazel et al. |
| 2005/0228385 A1 | 10/2005 | Iott et al. |
| 2006/0079892 A1 | 4/2006 | Roychowdhury et al. |
| 2008/0114362 A1 | 5/2008 | Justis et al. |
| 2008/0294202 A1* | 11/2008 | Peterson ............ A61B 17/7032 606/305 |
| 2010/0152787 A1 | 6/2010 | Walsh et al. |
| 2011/0040335 A1 | 2/2011 | Stihl et al. |
| 2011/0106173 A1 | 5/2011 | Lindemann et al. |
| 2011/0160779 A1 | 6/2011 | Schlaepfer et al. |
| 2012/0071926 A1 | 3/2012 | Jani et al. |
| 2014/0243900 A1 | 8/2014 | Ark et al. |
| 2015/0134006 A1 | 5/2015 | Ziolo et al. |
| 2015/0223844 A1 | 8/2015 | Leff et al. |
| 2015/0250512 A1 | 9/2015 | Poker et al. |
| 2015/0257792 A1 | 9/2015 | Jackson et al. |
| 2015/0359568 A1 | 12/2015 | Rezach |
| 2016/0051290 A1 | 2/2016 | Jackson et al. |
| 2016/0302831 A1 | 10/2016 | Nichols et al. |
| 2017/0095271 A1 | 4/2017 | Faulhaber |
| 2017/0311985 A1 | 11/2017 | Bobbitt et al. |
| 2018/0014863 A1 | 1/2018 | Biester et al. |

\* cited by examiner

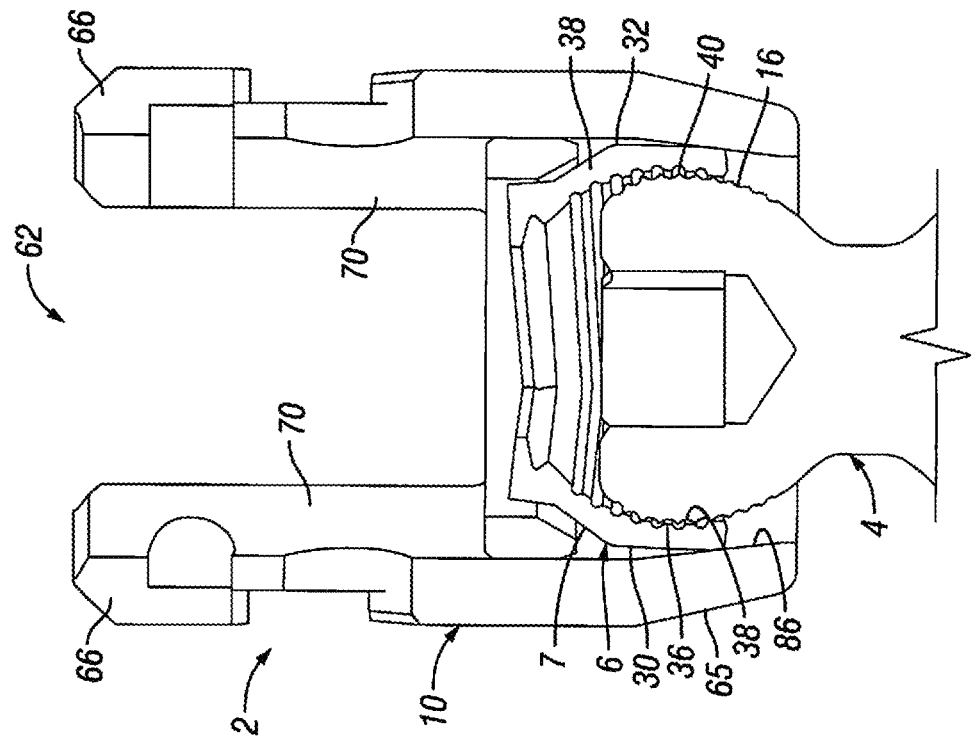
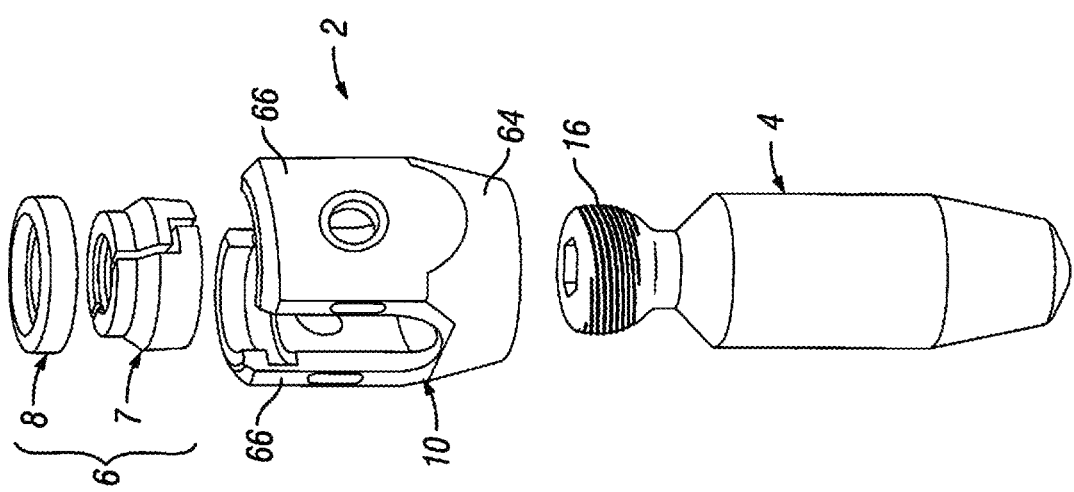

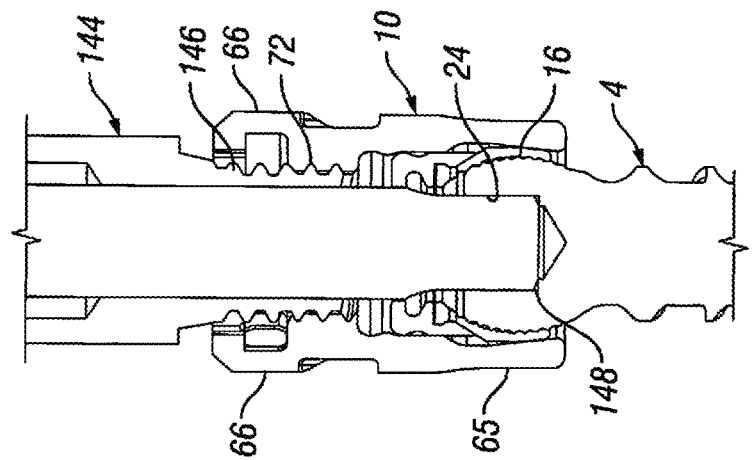
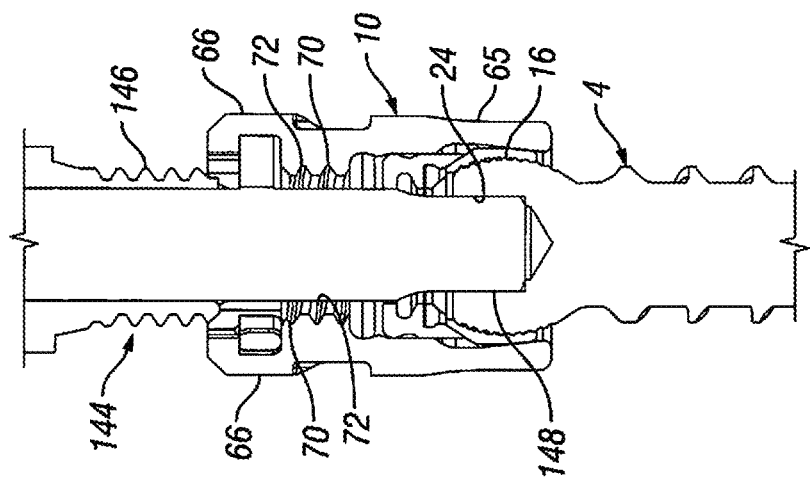
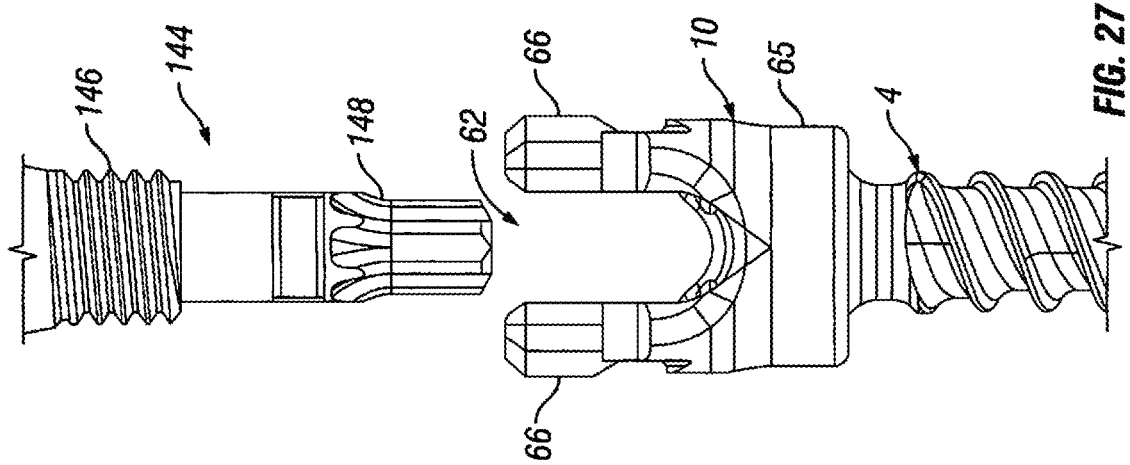

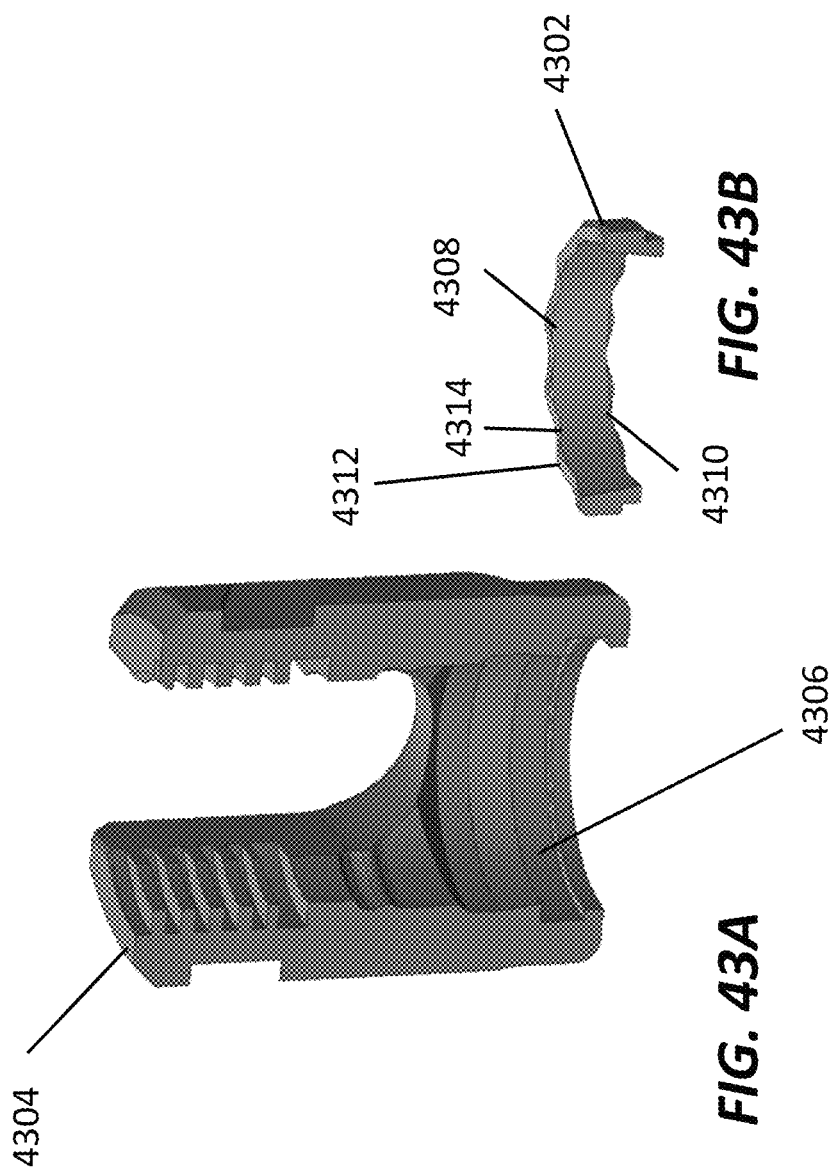

ORTHOPEDIC FIXATION DEVICES AND METHODS OF INSTALLATION THEREOF

CROSS REFERENCE TO RELATED APPLICATIONS

This application is a continuation of U.S. patent application Ser. No. 15/409,600, which is a continuation-in-part application of U.S. patent application Ser. No. 15/193,289 filed on Jun. 27, 2016, now U.S. Pat. No. 9,681,894, which is a continuation in part application of U.S. patent application Ser. No. 14/514,796 filed on Oct. 15, 2014, now U.S. Pat. No. 9,549,763, which is a divisional of U.S. patent application Ser. No. 13/183,965 filed on Jul. 15, 2011, now U.S. Pat. No. 8,888,827, the contents of all of which are incorporated by reference herein in their entireties for all purposes.

FIELD OF THE INVENTION

The present invention relates to orthopedic fixation devices, and, in one or more embodiments, to an orthopedic fixation device configured for loading of the bone fastener from the bottom of the tulip element.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine.

Treatment for these spinal irregularities often involves using a system of fixation devices to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, a fixation device along with a vertical solid member can help restore spinal elements to a pain free situation, or at least may help reduce pain or prevent further injury to the spine.

Typically, fixation devices may include a bone fastener (e.g., bone screw, hook, etc.) for coupling the fixation device to vertebra. Fixation devices further may include a tulip element for coupling the bone fastener to the elongated rod. Clamp and/or wedge elements may be used to secure the bone fastener in the tulip element. A locking cap may be used to secure the rod in the tulip element. While these designs can be used in the treatment of spinal irregularities, they typically require loading of the bone fastener from the top of the tulip element. One drawback to this top-loading design is that different sizes of the tulip element must be used based on the diameter of the bone fastener to accommodate passage of the fastener through the tulip element, as the inner bore of the tulip element will generally need to be larger than either the combined size of the bone fastener head and clamp element or the bone fastener diameter. Another drawback to this top-loading design is that bone hooks cannot be used as they will generally not pass through the tulip element. Yet another drawback to this top-loading design is that bone fastener must be installed in the bone while attached to the tulip element.

Accordingly, there exists a need for new and improved orthopedic fixation devices.

SUMMARY OF THE INVENTION

In an exemplary embodiment, the present disclosure provides an orthopedic fixation device including a coupling element, wherein the coupling element comprises a bore there through, a bone fastener, wherein the bone fastener comprises a head and an extension that extends from the head, wherein the head is configured for loading into the coupling element through the bottom of the bore. The orthopedic fixation device may also include a clamp configured to receive the head of the bone fastener, a saddle configured to engage the clamp and disposed on the clamp, and a retention member configured to engage the clamp, wherein the retention member includes an undulated top surface and an undulated bottom surface and further configured to be disposed in an indentation within the coupling element. The device may also, upon application of a force on top of the saddle, be configured such that the saddle presses the clamp to engage a tapered surface of the retention member to lock the coupling element to the bone fastener, and prior to the application of the force, the coupling element may be moved in a polyaxial manner with respect to the bone fastener.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 20-22 illustrate yet another alternative orthopedic fixation device in accordance with embodiments of the present invention;

FIGS. 27-29 illustrate a bone fastener having a threaded instrument interface in accordance with embodiments of the present invention.

FIG. 43A illustrates a cross-sectional views of an exemplary coupling element consistent with the principles of the present disclosure.

FIG. 43B illustrates a cross-sectional view of an exemplary retention member consistent with the principles of the present disclosure.

DETAILED DESCRIPTION OF THE PREFERRED EMBODIMENTS

Embodiments of the present invention are generally directed to orthopedic fixation devices configured for bottom loading of the bone fastener. Instead of loading the bone fastener from the top of the tulip element, embodiments of the present invention load the bone fastener from the bottom of the tulip element. With the bone fastener loaded in the tulip element, a locking clamp assembly can then be used to secure the bone fastener therein. Thus, unlike prior orthopedic fixation devices, embodiments of the present invention permit the use of larger bone fasteners without having to also increase the size of the tulip element. This should, for example, reduce the needed inventory, decreasing the necessary graphic cases needed to perform a similar procedure, while decreasing in-house inventory costs.

Further, as explained by the examples and illustrations below, the bone fastener of the orthopedic fixation devices can be placed in the vertebra without the tulip element in accordance with embodiments of the present invention. The tulip element can then be attached to the bone fastener in situ. This should reduce the material in the surgical wound, thus increasing visualization for disc preparation and interbody procedures, for example. The bone fastener can also be used to distract or otherwise manipulate the surgical site, further increasing visualization and ease of surgery, for example. Additionally, site preparation can be performed, in some embodiments, after the bone fastener has been placed, which may allow for more accurate pedicle decortication.

Figure 1:
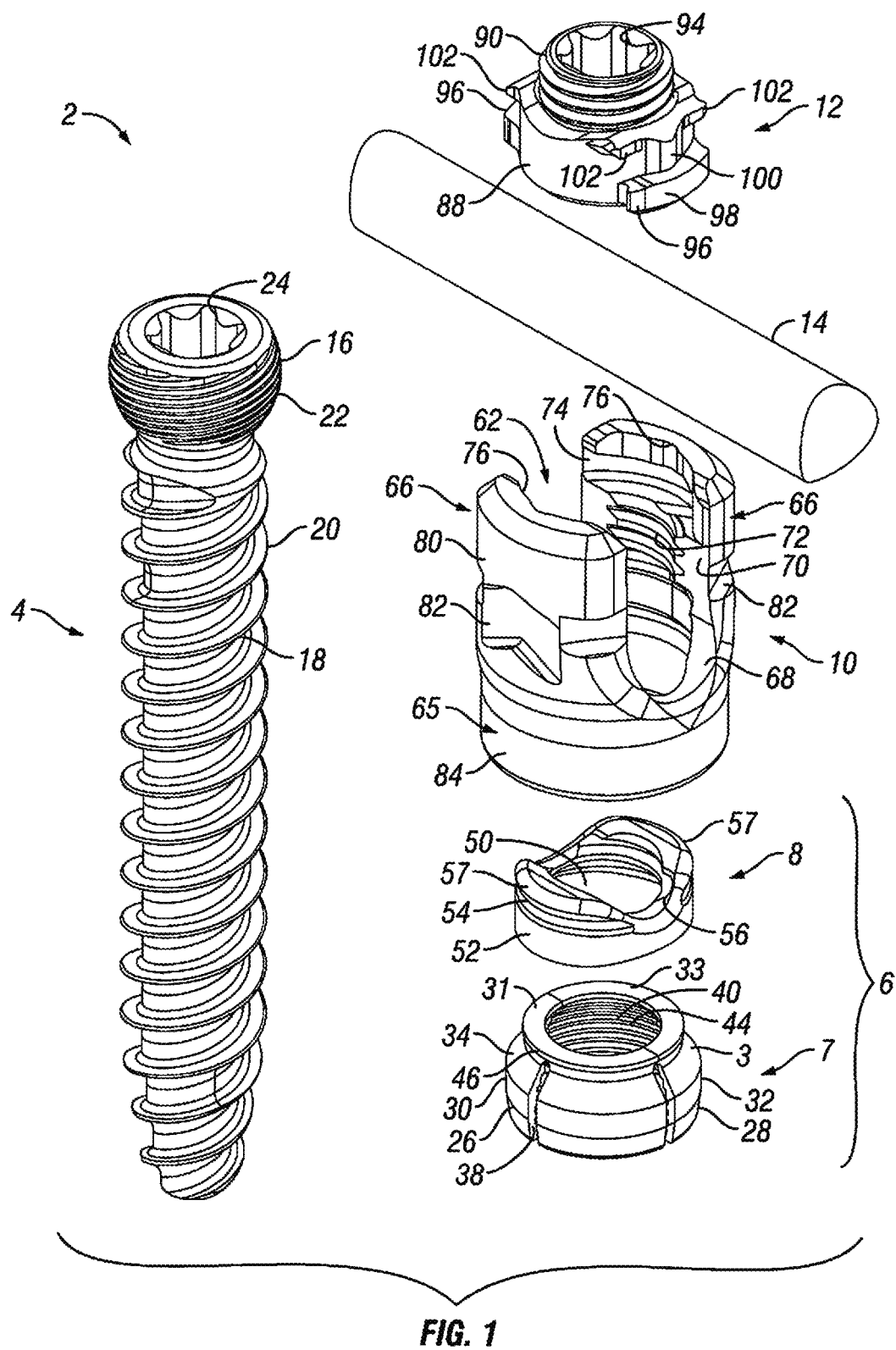
FIG. 1 is an exploded view of an orthopedic fixation device in accordance with embodiments of the present invention.

Turning now to FIG. 1, an exploded view of an orthopedic fixation device 2 is illustrated in accordance with embodiments of the present invention. As illustrated, the orthopedic fixation device 2 may comprise a bone fastener 4, a locking clamp assembly 6 (which may comprise, for example, a clamp element 7 and a wedge element 8), a tulip element 10, and a locking cap assembly 12. As will be discussed in more detail below, the bone fastener 4 may be loaded from the bottom of the tulip element 10 with the locking clamp assembly 6 already loaded therein. Prior to being locked into place, the tulip element 10 can be moved and rotated into a plurality of positions with respect to the bone fastener 4. Once the tulip element 10 is at the desired position with respect to the bone fastener 4, the tulip element 10 may be locked onto the bone fastener 4. In the illustrated embodiment, the locking cap assembly 12 is configured to secure a rod 14 in the tulip element 10. In one embodiment, the tulip element 10 is fixed onto the bone fastener 4 contemporaneously with securing of the rod 14 in the tulip element 10.

As illustrated by FIG. 1, the bone fastener 4 includes a head 16 and a shaft 18 that extends from the head 16. The illustrated embodiment shows the shaft 18 having a tapered shape and threads 20. Those of ordinary skill in the art will appreciate that the shaft 18 may have a number of different features, such as thread pitch, shaft diameter to thread diameter, overall shaft shape, and the like, depending, for example, on the particular application. While the head 16 may have any general shape, at least a portion of the head 16 may have a curved surface in order to allow for rotational movement or angular adjustment of the bone fastener 4 with respect to the tulip element 10. For example, at least a portion of the head 16 may be shaped to form a portion of a ball or at least a portion of a sphere. As illustrated, the head 16 may have a roughened or textured surface 22 that improves engagement with the clamp element 7. In certain embodiments, the head 16 may have a tool engagement surface, for example, that can be engaged by a screw-driving tool or other device. The tool engagement surface can permit the physician to apply torsional or axial forces to the bone fastener 4 to drive the bone fastener 4 into the bone. In the illustrated embodiment, the tool engagement surface of the head 16 is a polygonal recess 24. For instance, the polygonal recess 24 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

Figure 2:
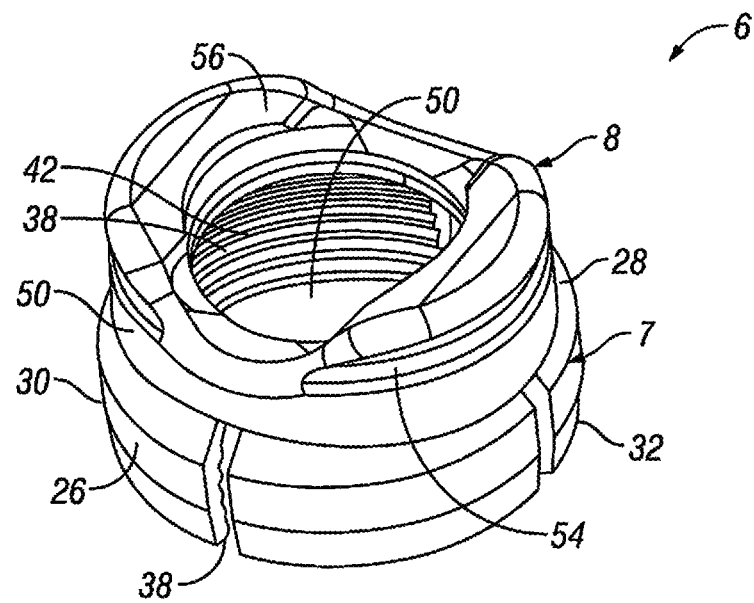
FIG. 2 is a perspective view of a locking clamp assembly in accordance with embodiments of the present invention.
Figure 3:
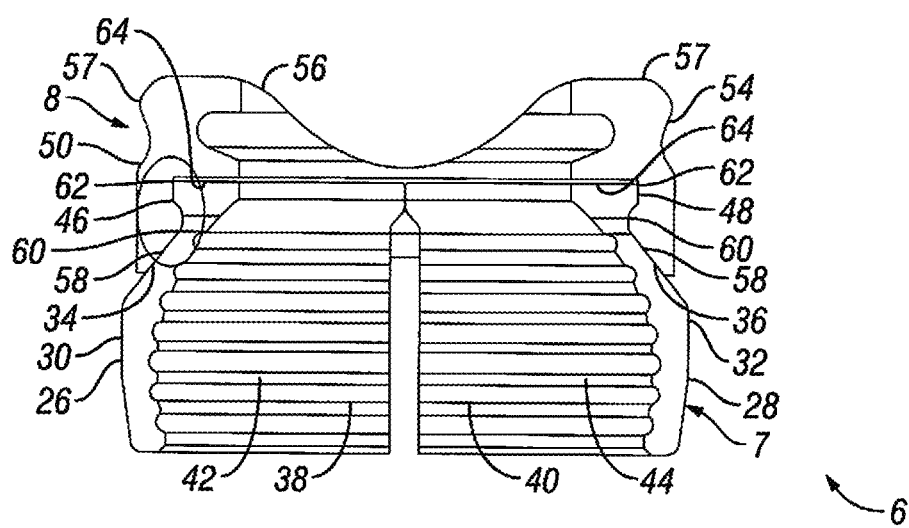
FIG. 3 is a cross-sectional view of a locking clamp assembly in accordance with embodiments of the present invention.

Referring now to FIGS. 1-3, clamp element 7 of the locking clamp assembly 6 will be described in more detail in accordance with embodiments of the present invention. As illustrated, the clamp element 7 includes a first clamp portion 26 and a second clamp portion 28. In the illustrated embodiment, the first clamp portion 26 is substantially identical to and a mirror image of, the second clamp portion 28. The first and second clamp portions 26, 28 provide a collar about the head 16 of the bone fastener 4, when installed, as discussed in more detail below. The first and second clamp portions 26, 28 grip bone fastener 4 when force is applied onto the clamp element 7 by the tulip element 10. While the embodiments that are described and illustrated generally describe the first and second clamp portions 26, 28 as substantially identical, the portions 26, 28 may be of varying size and are not required to be mirror images of one another. In addition, while the clamp element 7 is illustrated as having two clamp portions (first and second clamp portions 26, 28), the clamp element 7 may comprise more than two portions for gripping the bone fastener 4.

As illustrated, each of the first and second clamp portions 26, 28 includes an outer surface 30, 32, which may be curved or rounded, as best shown in FIGS. 1 and 2. The outer surfaces 30, 32 of the first and second clamp portions 26, 28 may each include an outer tapered surface 34, 36. In addition, the outer surfaces 30, 32 may each also have at least one slit 38 formed therein. The at least one slit 38 may, for example, allow the first and second clamp portions 26, 28 to constrict and securely engage the head 16 of the bone fastener 4. The outer surfaces 30, 32 should abut and engage the inner wedge surface 86 of the tulip element 10 when fully installed and locked in place in the tulip element 10 in accordance with present embodiments. With particular reference to FIG. 3, the first and second clamp portions 26, 28 each include inner surfaces 38, 40. When fully installed and locked in place in the tulip element 10, the inner surfaces 38, 40 should abut and engage the head 16 of the bone fastener 4 in accordance with present embodiments. The illustrated embodiment shows the inner surfaces 38, 40 having roughened or textured features 22 that improve engagement with the head 16 of the bone fastener 4. The first and second clamp portions 26, 28 each may also include an external lip 46, 48, which may be located above the outer tapered surfaces 34, 36, as best seen in FIG. 3. The first and second clamp portions 26, 28 each may also include an upper surface 31, 33, as best seen in FIG. 1.

Figure 4:
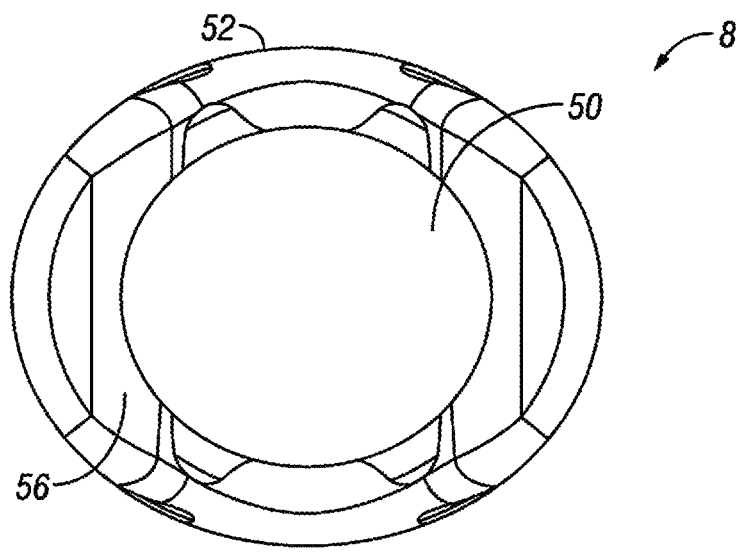
FIG. 4 is a top view of a wedge element in accordance with embodiments of the present invention.
Figure 5:
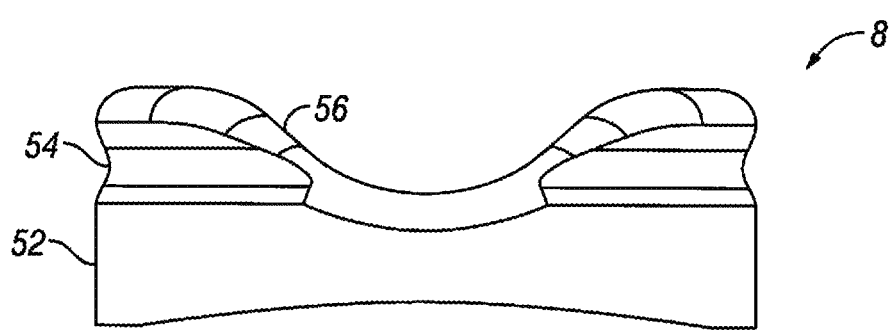
FIG. 5 is a side view of a wedge element in accordance with embodiments of the present invention.

Referring now to FIGS. 1-5, the wedge element 8 of the locking clamp assembly 6 will be described in more detail in accordance with embodiments of the present invention. As illustrated, the wedge element 8 may include a bore 50. The lower portion of the bore 50 may be sized to receive the upper portion of the clamp element 7, including external lips 46, 48 of the first and second clamp portions 26, 28. The wedge element further may include an outer surface 52 having a recessed portion 54. The outer surface 52 may be generally rounded, for example. As best seen in FIG. 4, the outer surface 52 of the wedge element 8 may be generally elliptical, in one embodiment. The elliptical shape of the outer surface 52 should, for example, limit radial motion of the wedge element when installed in the tulip element 10. The wedge element 8 further may include an upper surface 56. In the illustrated embodiment, the upper surface 56 defines a seat that receives the rod 14. As illustrated, the upper surface 56 may be generally convex in shape. In the illustrated embodiment, the wedge element 8 further includes an upper lip 57.

With particular reference to FIG. 3, the wedge element 8 further includes an inner wedge surface 58. As illustrated, the inner wedge surface 58 may be disposed around a lower portion of the bore 50. In one embodiment, the inner wedge surface 58 forms a conical wedge. The inner wedge surface 58 operates, for example, to engage the outer tapered surfaces 34, 36 of the first and second clamp portions 26, 28 to force the clamp element 7 down the bore 62 of the tulip element 10. The wedge element 8 further may include an inner protruding surface 60 adjacent to the inner wedge surface 58 and an inner recessed surface 62 adjacent the inner protruding surface 60. The wedge element 8 further may include an inner seat 64. As illustrated, the inner seat 64 may be downwardly facing for receiving upper surfaces 31, 33 of the first and second clamp portions 26, 28. In an embodiment, the inner seat 64 restricts or limits movement of the clamp element 4 through the bore 50 of the wedge element 8.

In accordance with present embodiments, the locking clamp assembly 6 can be assembled prior to insertion into the tulip element 10. In one embodiment, for assembly, the clamp element 7 may be inserted into the wedge element 8 upwardly through the bore 50. The outer surfaces 30, 32 of the first and second clamp portions 26, 28 should slidingly engage the inner wedge surface 58 of the wedge element 8 as the clamp element 7 is inserted. The clamp element 7 should be inserted until the external lips 46, 48 of the first and second clamp portions 26, 28 pass the inner protruding surface 60 of the wedge element 8. The inner protruding surface 60 engages the external lips 46, 48 to secure the clamp element 7 in the wedge element 8. In the illustrated embodiment, the locking clamp assembly 6 will not fit downwardly through the top of the bore 62 of the tulip element 10 as the locking clamp assembly has an outer diameter at its biggest point that is larger than the inner diameter of the upper portion of the bore 62.

Figure 6:
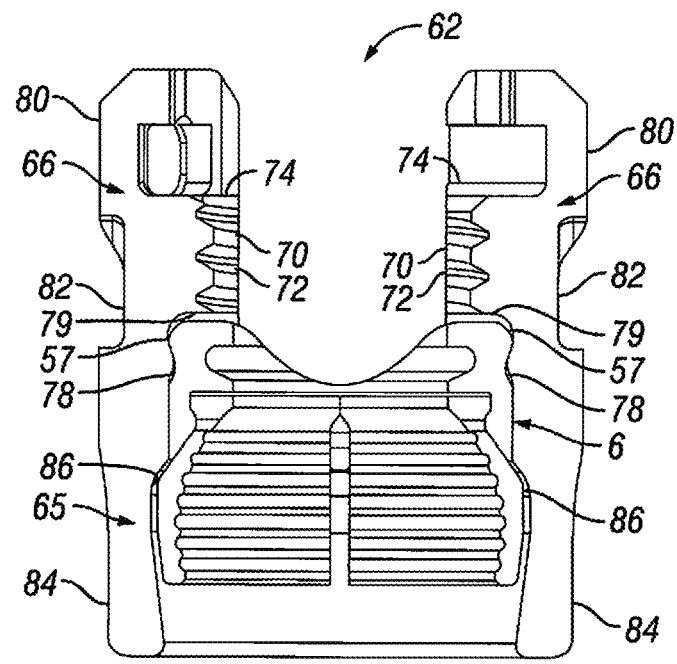
FIG. 6 is a cross-sectional view of a locking clamp assembly disposed in a tulip element in an unlocked configuration in accordance with embodiments of the present invention.
Figure 9:
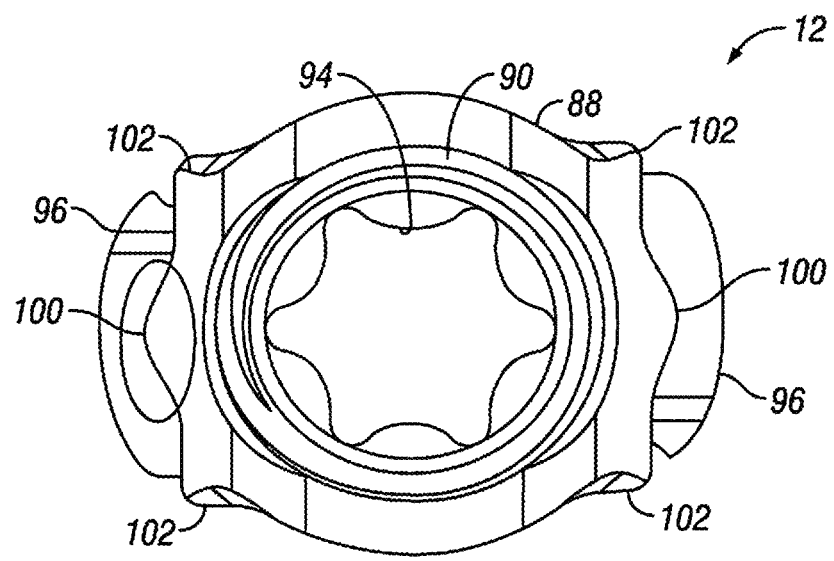
FIG. 9 is a top view of a locking cap assembly in accordance with embodiments of the present invention.
Figure 8:
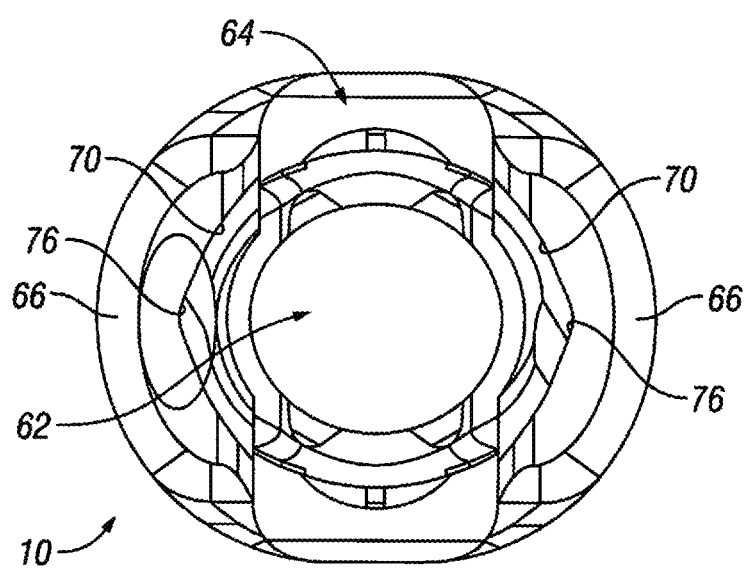
FIG. 8 is a top view of a tulip element in accordance with embodiments of the present invention.
Figure 10:
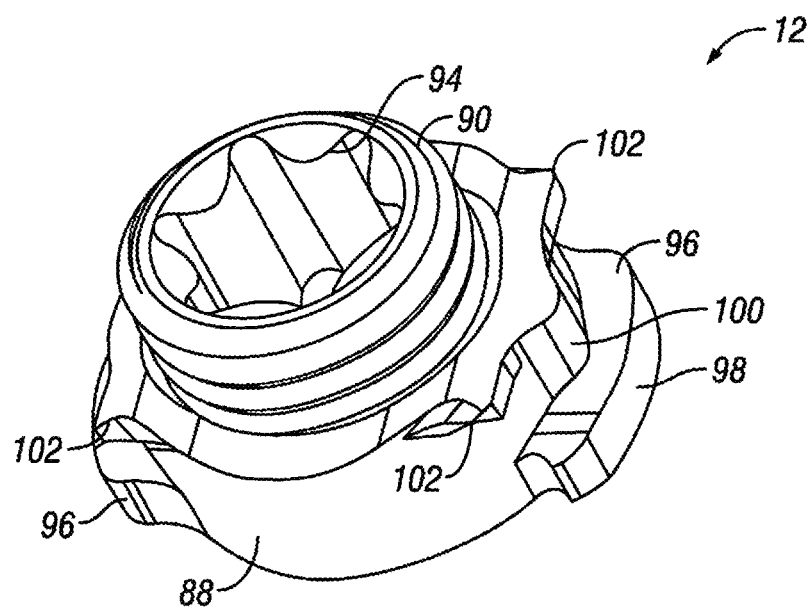
FIG. 10 is a perspective view of a locking cap assembly in accordance with embodiments of the present invention.
Figure 11:
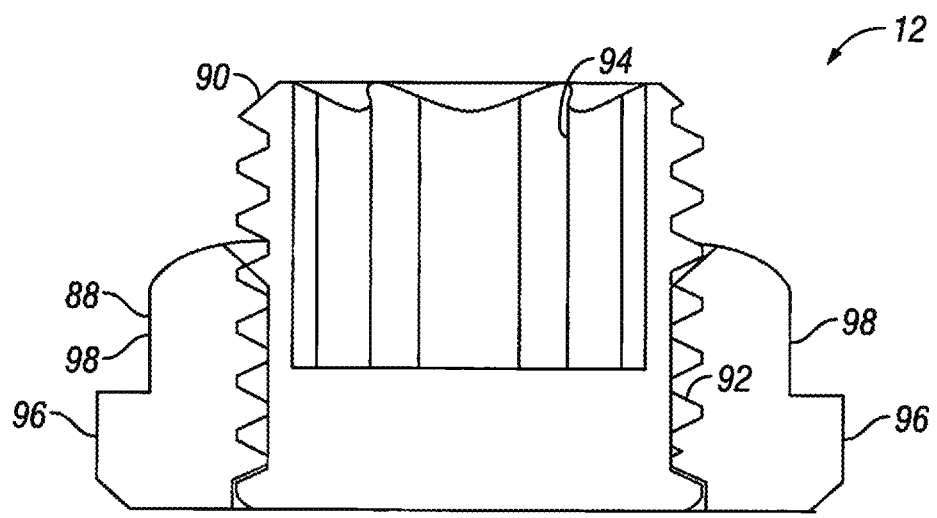
FIG. 11 is a cross-sectional view of a locking cap assembly in accordance with embodiments of the present invention.

Referring now to FIGS. 1 and 6-8, the tulip element 10 will be described in more detail in accordance with embodiments of the present invention. As illustrated, the tulip element 10 may comprise bore 62, a body 65 and arms 66 that extend upwardly from the body 65. In the illustrated embodiment, the arms 66 define a U-shaped channel 68 sized to receive the rod 14. Each of the arms 66 has an interior surface 70 the interior surface 70 having a threaded portion 72 for engaging corresponding threads on a screw-driving tool (e.g., tool 144 on FIGS. 27-29). The interior surface 70 of each of the arms 66 further may include a slot 74 for receiving corresponding tabs 96 (e.g., FIG. 9) of the locking cap assembly 12 and a recessed surface 76 for engaging corresponding protuberances 100 (e.g., FIG. 9) of the locking cap assembly 12. As illustrated, the recessed surface 76 of each of the arms 66 may be located above the slot 74. The interior surface 70 of each of the arms 66 further may include a protuberance 78. In the illustrated embodiment, the protuberance 78 of each of the arms 66 is located below the threaded portion 72 with the threaded portion 72 being located between the protuberance 78 and the slot 74. As best seen in FIG. 6, the interior surface 70 of each of the arms 66 further may form a downwardly facing seat 79, for example, which may limit or restrict movement of the locking clamp assembly 6 through the bore 62. Each of the arms 66 further may include an outer surface 80. The outer surface 80 of each of the arms 66 may include a tool engagement groove 82 formed on the outer surface 80 which may be used for holding the tulip element 10 with a suitable tool (not illustrated).

Figure 7:
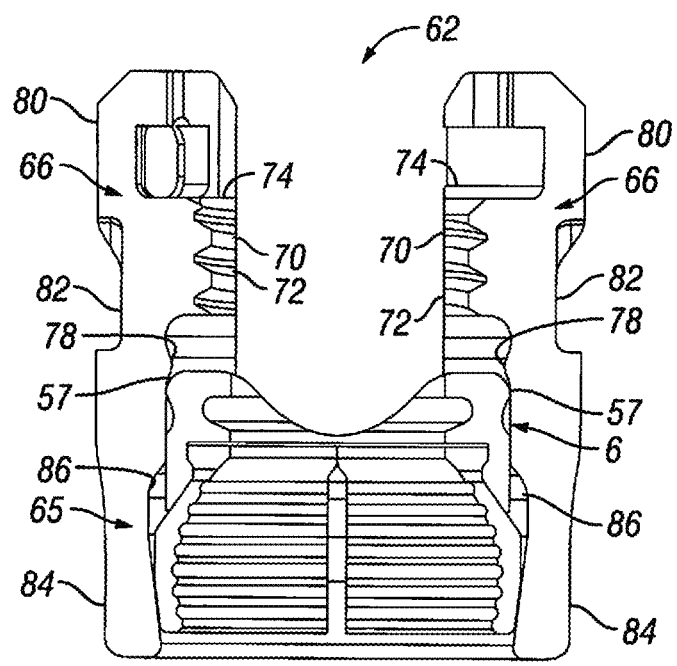
FIG. 7 is a cross-sectional view of a locking clamp assembly disposed in a tulip element in a locked configuration in accordance with embodiments of the present invention.

As illustrated, the body 65 of the tulip element 10 may have an outer surface 84, which may be curved or rounded, as best seen in FIG. 1. With particular reference to FIGS. 6 and 7, the body 65 further may include an inner wedge surface 86 disposed around a lower portion of the bore 62. In one embodiment, the inner wedge surface 86 forms a conical wedge. The inner wedge surface 86 of the body 65 of the tulip element 10, for example, may abut and engage the outer surfaces 30, 32 of the first and second clamp portions 26, 28 when the locking clamp assembly 6 is fully installed and locked in place.

In accordance with present embodiments, the locking clamp assembly 6 may be installed in the tulip element 10 in either an unlocked position or a locked position. FIG. 6 illustrates the locking clamp assembly 6 disposed in the tulip element 10 in the unlocked position in accordance with embodiments of the present invention. In FIG. 6, the locking clamp assembly 6 has been inserted into the tulip element 10 upwardly through the bore 62. The locking assembly 6 should be inserted until the upper lip 57 of the wedge element 8 passes the protuberances 78 located on the interior surfaces 70 of the arms 66 of the tulip element 10. The protuberances 78 should engage the upper lip 57 to secure the locking clamp assembly 6 in the tulip element 10. While not illustrated on FIG. 6, the bone fastener 4 (e.g., shown on FIG. 1) can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. The locking clamp assembly 6 should also move with the tulip element during rotation of the tulip element 10 with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 7 illustrates the locking clamp assembly 6 disposed in the tulip element 10 in the locked position in accordance with embodiments of the present invention. In FIG. 7, the locking clamp assembly 6 has been pushed downwardly in the bore 62 of the tulip element 10. As illustrated, the locking clamp assembly 6 has been pushed downward until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 (e.g., FIG. 1). In the locked position, tulip element 10 should be locked onto the bone fastener 4, thus preventing further positioning of the tulip element 10 with respect to the bone fastener 4.

Referring now to FIGS. 1 and 9-11, the locking cap assembly 12 will be described in more detail in accordance with embodiments of the present invention. As illustrated, the locking cap assembly 12 may comprise a body 88 and a set screw 90 threaded into a bore 92 in the body 88. The set screw 90 may have a length, for example, that is longer than the length of the bore 92. In the illustrated embodiment, at least a portion of the set screw 90 extends from the top of the body 88. In certain embodiments, the set screw 90 may have a tool engagement surface, for example, that can be engaged by a screw-driving tool or other device. The tool engagement surface can permit the physician to apply torsional or axial forces to the set screw 90 to advance the set screw 90 through the body 88 and onto the rod 14. When the locking cap assembly 12 is in its locked position, the set screw 90 can be advanced through the body 88 to engage the rod 14, applying downward force onto the rod 14 and securing it to the tulip element 12. In one embodiment, the set screw 90 forces the rod 14 downward and into contact with the locking clamp assembly 6 causing the locking cap assembly 6 to move downward in the tulip element 10. In the illustrated embodiment, the tool engagement surface of the set screw 90 is a polygonal recess 94. For instance, the polygonal recess 94 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

In accordance with present embodiments, the body 88 may have one or more projections. For example, the body 88 may comprise lower tabs 96 projecting radially from a lower end of the body 88. In the illustrated embodiment, the body 88 comprises a pair of lower tabs 96 located on opposite sides of the body 88. As illustrated, the lower tabs 96 may each have an outer surface 98 that is generally rounded in shape. In addition, while the body 88 is illustrated as having two lower tabs 96, the body 88 may comprise more than two lower tabs 96. As illustrated, the body 88 further may comprise protuberances 100. The protuberances 100 may engage with corresponding recessed surface 76 (e.g., FIG. 10) of the arms 66 of the tulip element 10. The protuberances 100 may be capable of providing a tactile or audible signal to the physician, such as a click that may be felt or heard, when the locking cap assembly 12 has reached its locking position. The protuberances 100 also may assist in maintaining the locking cap assembly 12 in its locked position. In the illustrated embodiment, the body 88 further may comprise tool engagement features. The tool engagement features may, for example, be used for holding or manipulating the locking cap assembly 12 with a suitable tool (not illustrated). In the illustrated embodiment, the locking cap assembly 12 includes upper tabs 102. As illustrated, the tabs 102 may be formed at the upper surface of the body 88. In the illustrated embodiment, the locking cap assembly 12 includes four upper tabs 102 at the corners of the upper surface. In addition, while the body 88 is illustrated as having four upper tabs 102, the body 88 may comprise more or less than four upper tabs 102.

To place the locking cap assembly 12 onto the tulip element 10, the lower tabs 96 should be aligned with the u-shaped channel 68 formed by the arms 66 of tulip element 10 and the locking cap assembly 12 can then be lowered downward into the bore 62 in the tulip element 10. Once the lower tabs 96 are aligned with the corresponding slots 74 in the arms 66 of the tulip element 10, the locking cap assembly 12 can be rotated. The slots 74 allow the lower tabs 96 to pass through the arms 66 when the lower tabs 96 and the slots 74 are aligned. The length of the slots 74 generally correspond to the amount of rotation needed to move the locking cap assembly 12 into or out of a locked position. In one embodiment, the locking cap assembly 12 rotates from about 60° to about 120° for placement into a locking positions, alternatively, about 80° to about 100°, and, alternatively, about 90°. As previously mentioned, the protuberances 100 can be configured to provide a tactile or audible signal to the physician when the locking cap assembly 12 has reached its locked assembly. In addition, the protuberances 100 can also assist in maintaining the locking cap assembly 12 in its locked position. Other features such as undercuts and geometric mating surfaces may be used to prevent rotation in the opposite direction. With the locking cap assembly 12 locked in place, the set screw 94 can then be rotated. As the set screw 94 moves downward and extends from the bottom of the base 88 of the locking cap assembly 12, the set screw 94 presses against the rod 14 securing it in the tulip element 10. In addition, the rod 14 may also be pressed downward into engagement with the locking clamp assembly 6 forcing it downward in the tulip element 10. As the locking clamp assembly 6 moves downward, the clamp element 7 engages the body 65 of the tulip element 10. As best seen in FIG. 7, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 and secure it with respect to the tulip element 10.

Figure 12:
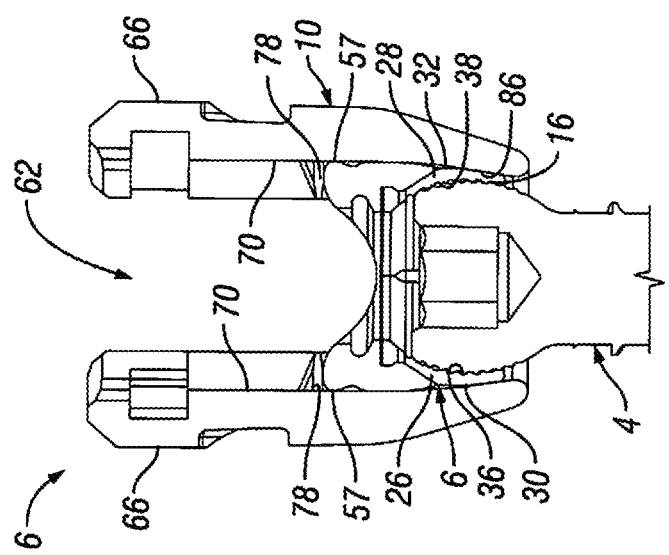
FIGS. 12-14 illustrate an alternative orthopedic fixation device in accordance with embodiments of the present invention.
Figure 13:
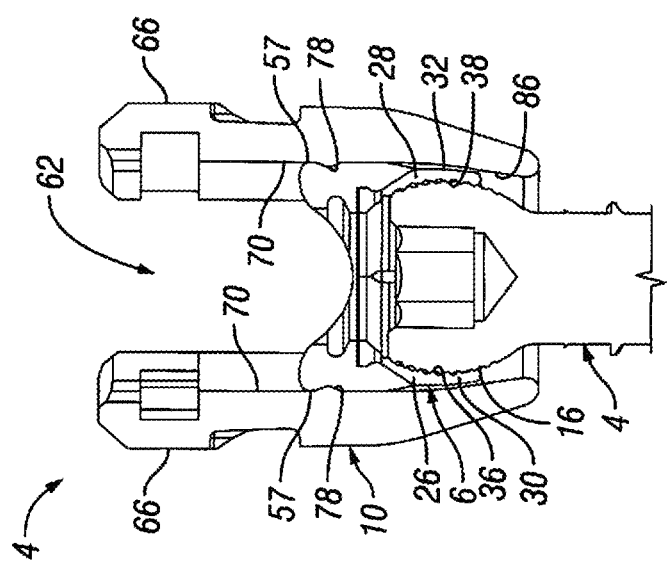
Figure 14:
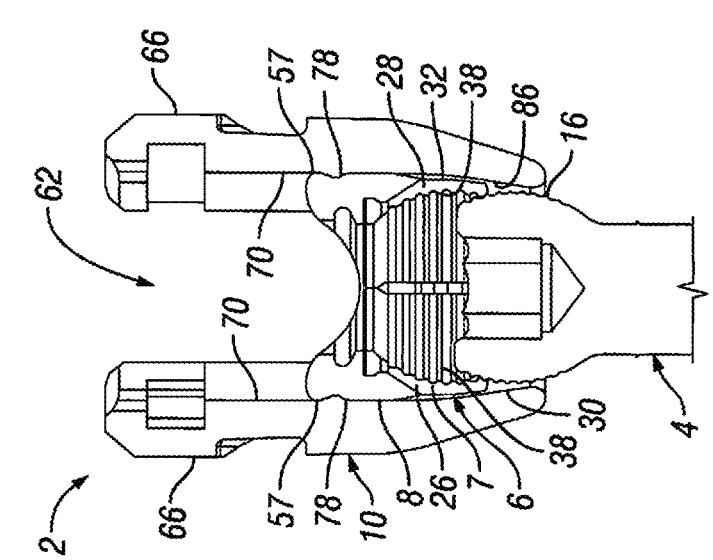

Referring now to FIGS. 12-14, locking of the tulip element 10 onto the bone fastener 4 is illustrated in more detail in accordance with embodiments of the present invention. For the purposes of this illustration, the locking cap element 12 (e.g., FIG. 1) is not shown. The tulip element 10 shown in FIGS. 12-14 is similar to the tulip element 10 described previously except that the tulip element 10 does not include a threaded portion 72 (e.g., FIGS. 6-7) or a downwardly facing seat 79 (e.g., FIG. 6) in the interior surface 70 of the arms 66 of the tulip element 10. FIG. 12 illustrates the locking clamp assembly 6 installed in the tulip element 10 in an unlocked position. As previously mentioned, the locking clamp assembly 6 can be inserted into the tulip element 10 upwardly through the bore 62. As shown in FIG. 12, the locking assembly 6 should be inserted until the upper lip 57 of the wedge element 8 passes the protuberances 78 located on the interior surfaces 70 of the tulip element 10. The protuberances 78 should engage the upper lip 57 to secure the locking clamp assembly 6 in the tulip element 10. As illustrated by FIG. 13, the bone fastener 4 can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 14 illustrates the locking clamp assembly 6 disposed in the tulip element 10 in the locked position and clamping onto the bone fastener 4 to secure the bone fastener 4 with respect to the tulip element 10 in accordance with embodiments of the present invention. As seen in FIG. 14, the locking clamp assembly 6 has been pushed downwardly in the bore 62 of the tulip element 10 until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4. In the locked position, tulip element 10 should be locked onto the bone fastener 4, thus preventing further positioning of the tulip element 10 with respect to the bone fastener 4.

Figure 15:
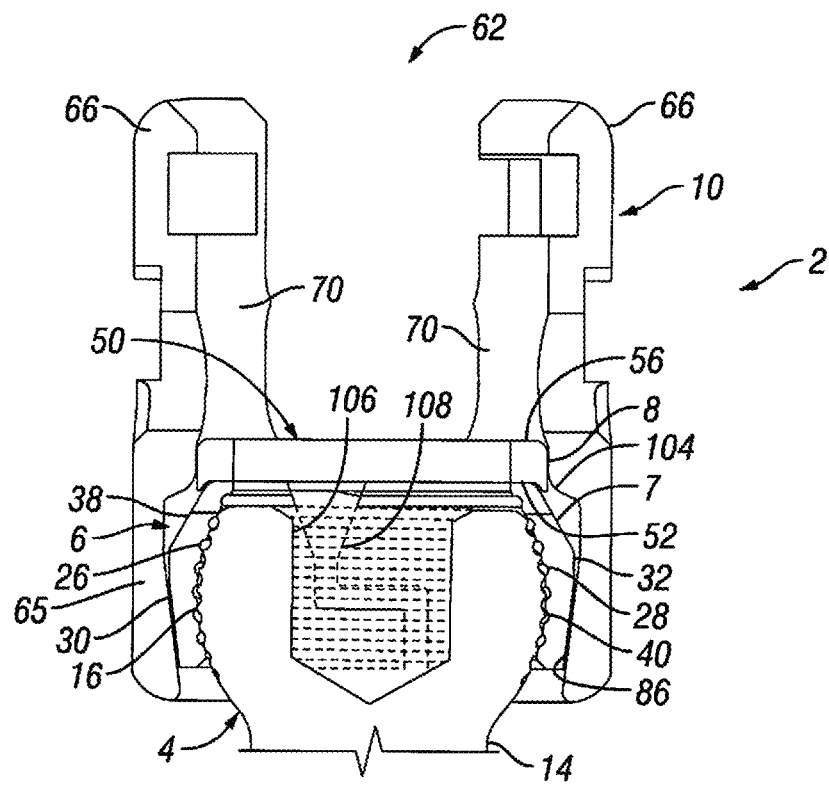
FIGS. 15-16 illustrate another alternative orthopedic fixation device in accordance with embodiments of the present invention.
Figure 16:
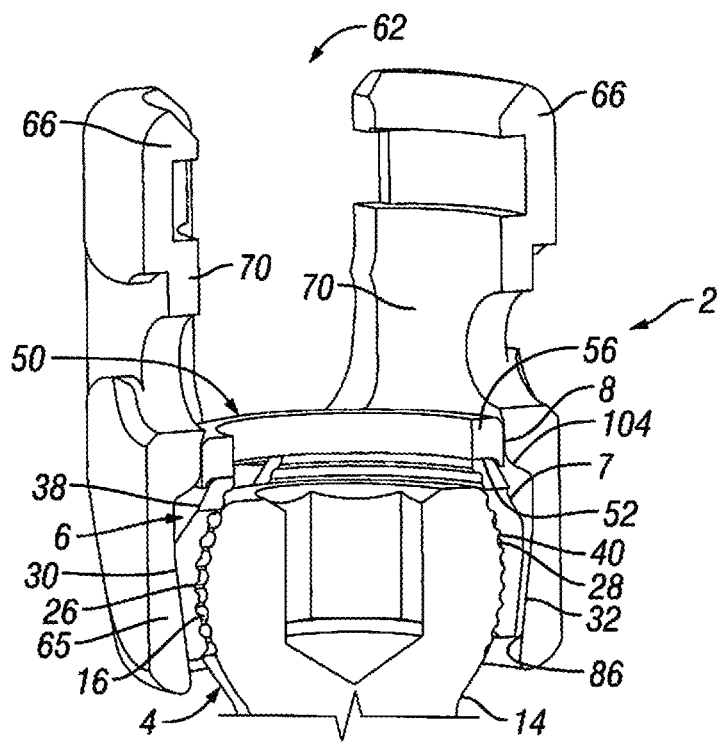

Referring now to FIGS. 15 and 16, an orthopedic fixation device 2 is described in accordance with alternative embodiments of the present invention. As illustrated, the orthopedic fixation device 2 comprises a bone fastener 4, locking clamp assembly 6, and a tulip element 10. For the purposes of this illustration, the locking cap assembly 12 (e.g., FIG. 1) is not shown. As previously mentioned, the locking clamp assembly 6 comprises a clamp element 7 and a wedge element 8. As illustrated, the clamp element 7 may include a first clamp portion 26 and a second clamp portion 28. In the illustrated embodiment, the first and second clamp portions 26, 28 each include an inner tapered surface 106, 108 such that the lower portions of the first and second clamp portions 26, 28 can expand when pressure is applied that constricts the upper portion of the first and second clamp portions 26, 28. In contrast, to the wedge element 8 that was previously described, embodiments of the upper surface 56 of the wedge element 8 illustrated on FIGS. 15 and 16 do not define a seat that receives the rod 14 (e.g., FIG. 1), but rather are generally planar with bore 50 penetrating there through. As illustrated, the wedge element 8 further includes an inner wedge surface 58 formed around a lower portion of the bore 50. As also previously mentioned, the tulip element 10 generally may comprise a bore 62, base 64, and arms 66. The inner diameter of the bore 62 in the upper portion of the tulip element 10 may be made smaller than either the combined size of the clamp element 7 and the bone fastener 4 or the diameter of the shaft 14 of the bone fastener 4, whichever is larger. As illustrated, the arms 66 may each comprise an interior surface 70. In the illustrated embodiment, the interior surface 70 includes inner tapered surface 104 rather than a downwardly facing seat 79 (e.g., FIG. 6) in the interior surface 70 of the arms 66 of the tulip element 10.

With continued reference to FIGS. 15 and 16, locking of the tulip element 10 onto the bone fastener 4 will be described in more detail in accordance with embodiments of the present invention. The first and second clamp portions 26, 28 of the clamp element 7 may be inserted one after another upwardly into the bore 62 of the tulip element 10. The first and second clamp portions 26, 28 may be pushed axially towards the top of the tulip element 10. The first and second clamp portions 26, 28 should continue to move upwardly until they engage the inner tapered surface 104 of the tulip element 10. Due the taper angle of the inner tapered surface 104, the upper portion of the first and second clamp portions 26, 28 will be forced to move inwards until the inner tapered surfaces 106, 108 of each of the first and second clamp portions 26, 28 come into contact. This contraction at the top of the first and second clamp portions 26, 28 should result in a wider opening at the bottom of the clamp element 7. The bone fastener 4 can then be inserted through the bottom of the bore 62 of the tulip element 10 and into the clamp element 7. The bone fastener 4 can then be manipulated, for example, to center the clamp element 7 into the head 16 of the bone fastener 4. The tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4.

To lock the tulip element 10, the bone fastener 4 can be pulled downward and because the clamp element 7 is in engagement with the bone fastener 4, the clamp element 7 should also move downward in the tulip element 10 such that the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 17:
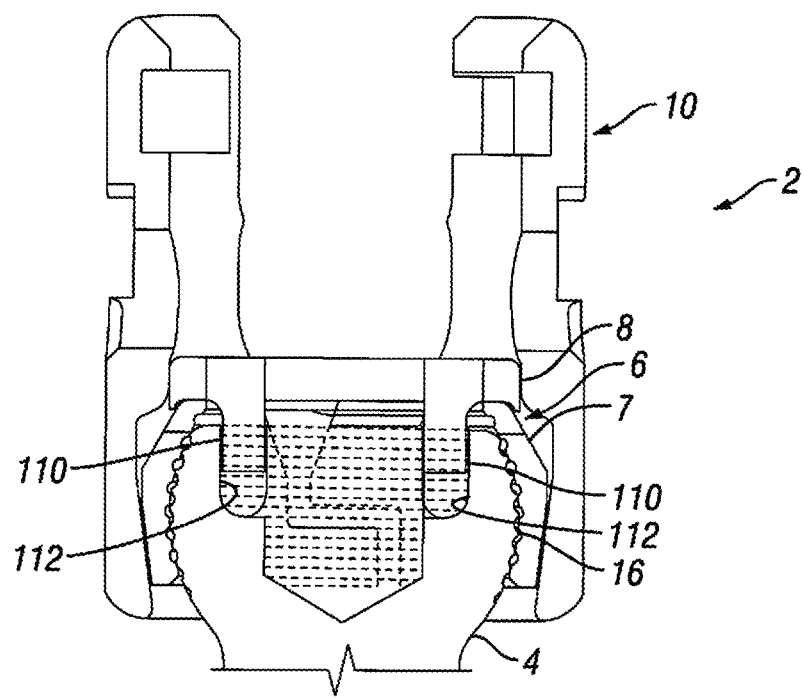
FIGS. 17-19 illustrate yet another alternative orthopedic fixation device in accordance with embodiments of the present invention.
Figure 18:
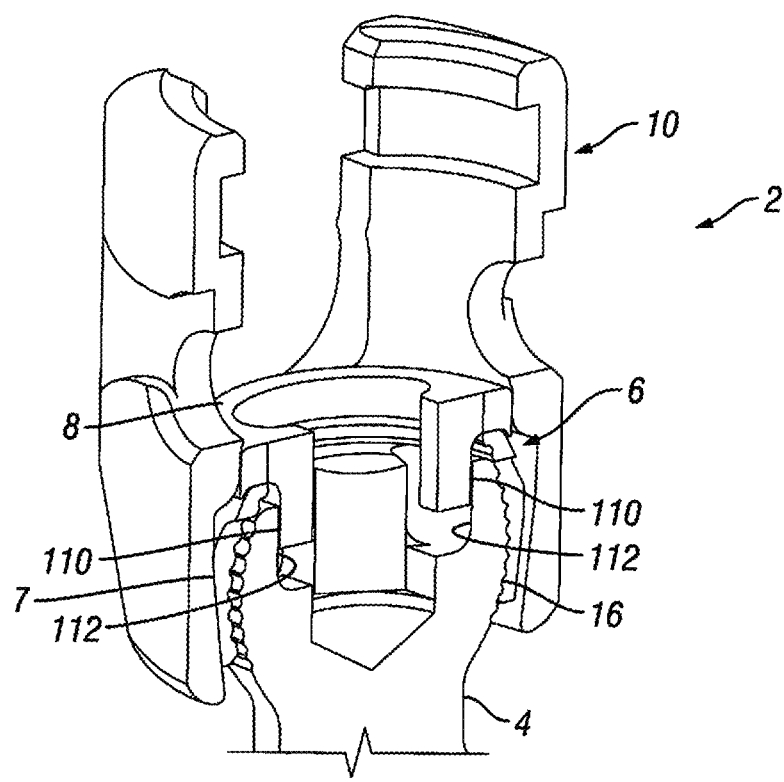
Figure 19:
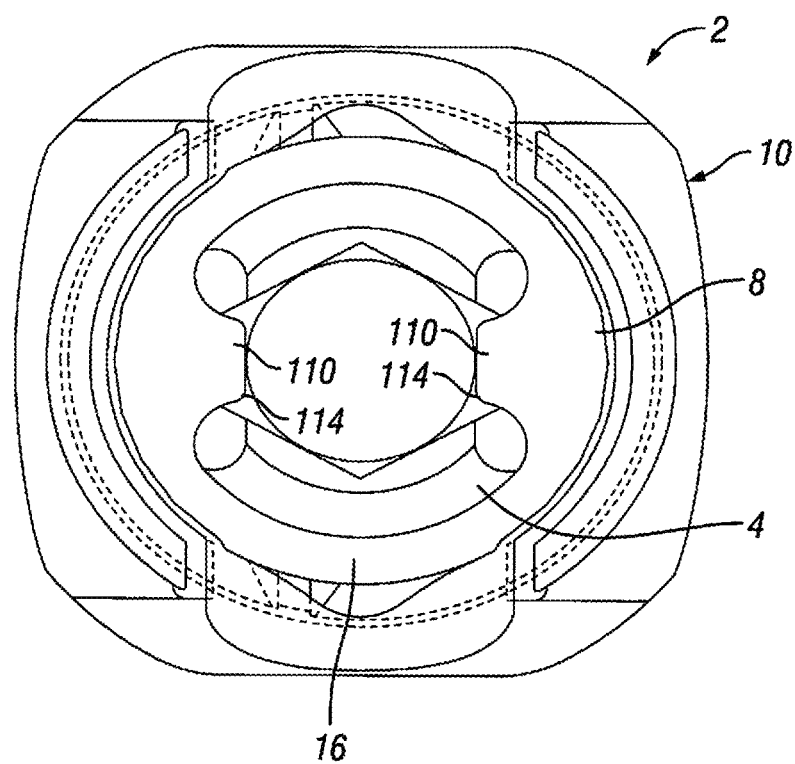

Referring now to FIGS. 17-19, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8. The orthopedic fixation device 2 is similar to the embodiments of FIGS. 15-16 except that embodiments of the wedge element 8 include downwardly extending tabs 110 that fits into corresponding slots 112 in the top of the head 16 of the bone fastener 4. In general, the tabs 110 should impart a uni-planar restraint on the bone fastener 4 so that it only slides along mating surfaces. The interior surfaces 114 of the tabs 110, best seen in FIG. 19, should forms the sides of the internal driving features. In an alternative embodiment (not illustrated), the wedge element 8 can be configured so that the tabs 110 are interconnected, for example, to impart more strength to the design of the wedge element 8.

Referring now to FIGS. 20-21, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8.

The orthopedic fixation device 2 is similar to the embodiments of FIGS. 15-16 except that embodiments of the clamp element 7 are configured for top loading from the top of the bore 62 in the tulip element 10. Instead of being inserted upwardly from the bottom of the bore 62, the first and second clamp portions 26, 28 of the clamp element 7 are inserted downwardly from the top of the bore 62, until the clamp portions 26, 28 engage the inner wedge surface 86 of the body 65 of the tulip element 10. The bone fastener 4 can then be inserted upwardly from the bottom of the bore 62 of the tulip element 10 and into engagement with the clamp element 7 whereby the clamp element 7 will be pushed upwardly towards the top of the tulip element 10. The clamp element 7 will move higher until they engage an external temporary stop (not illustrated) that prevents further upward movement. As the clamp element 7 moves higher in the tulip element 10, the clamp portions 26, 28 adjust and reorient due to increased clearance with the inner wedge surface 86 of the tulip element 10 such that the opening at the bottom of the clamp element 7 is larger than the diameter of the head 16 of the bone fastener 4.

To lock the tulip element 10, the bone fastener 4 can be pulled downward and because the clamp element 7 is in engagement with the bone fastener 4, the clamp element should also move downward in the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. In accordance with present embodiments, the smallest inner diameter for the bore 62 in the tulip element 10 is smaller than the combined size of the clamp element 7 and the head 16 of the bone fastener 4, when in engagement. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 22:
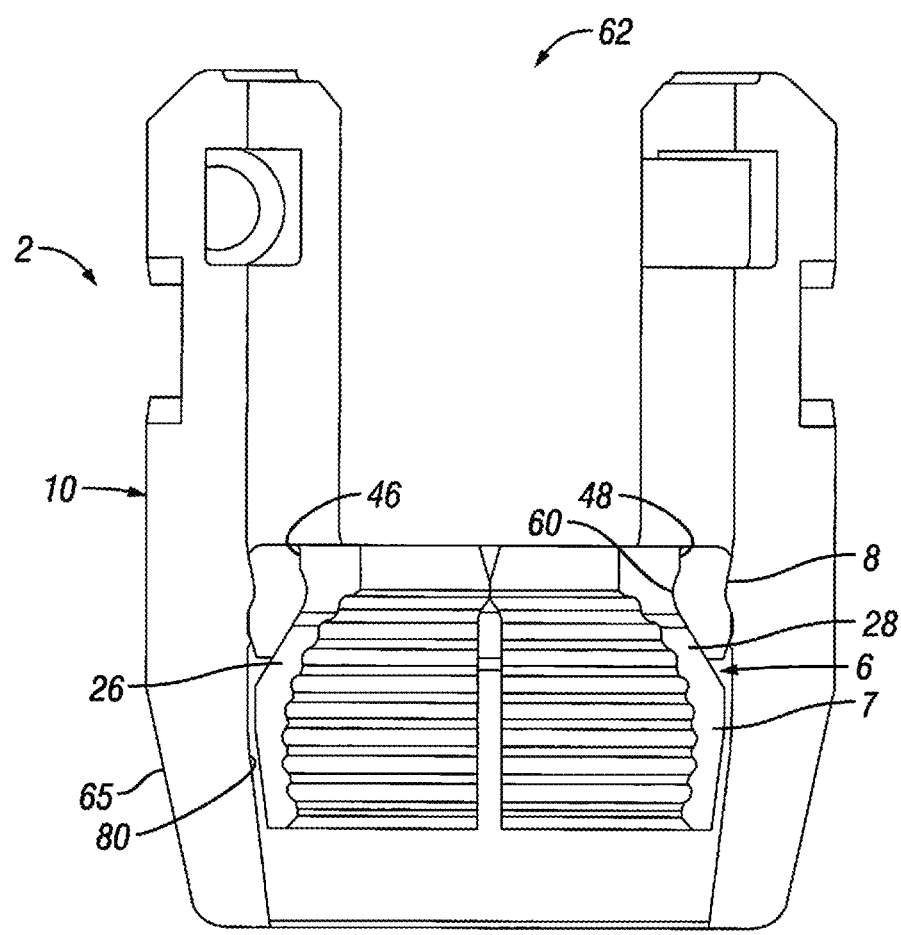

Referring now to FIG. 22, an orthopedic fixation device 2 is described in accordance with alternative embodiments of the present invention. As illustrated, the orthopedic fixation device 2 comprises a locking clamp assembly 6 and a tulip element 10. For the purposes of this illustration, the bone fastener (e.g., FIG. 1) and locking cap assembly 12 (e.g., FIG. 1) are not shown. In the illustrated embodiment, the locking clamp assembly 6 comprises a clamp element 7 and a wedge element 8.

The orthopedic fixation device 2 is similar to the embodiments of FIGS. 20-21 except that embodiments of the wedge element 8 include a retention feature for coupling with the clamp element 7. As illustrated, the wedge element 8 includes an inner protruding surface 60 that engages with the external lips 46, 48 of the first and second clamp portions 26, 28 of the clamp element 7 to secure the clamp element 7 in the wedge element 8. The locking clamp assembly 6 with the clamp element 7 secured in the wedge element 8 can then be inserted downwardly from the top of the bore 62 in the tulip element 10, until the clamp portions 26, 28 engage the inner wedge surface 86 of the body 65 of the tulip element 10. Once the bone fastener 4 is snapped into the clamp element 7, the locking clamp assembly 6 can be forced downwards through the tulip element 10 into its locked position to secure the bone fastener (e.g., FIG. 1) in the clamp element 7. In the locked position, the tulip element 10 should be locked onto the bone fastener 4, thus preventing further positioning of the tulip element 10 with respect to the bone fastener 4.

Figure 23:
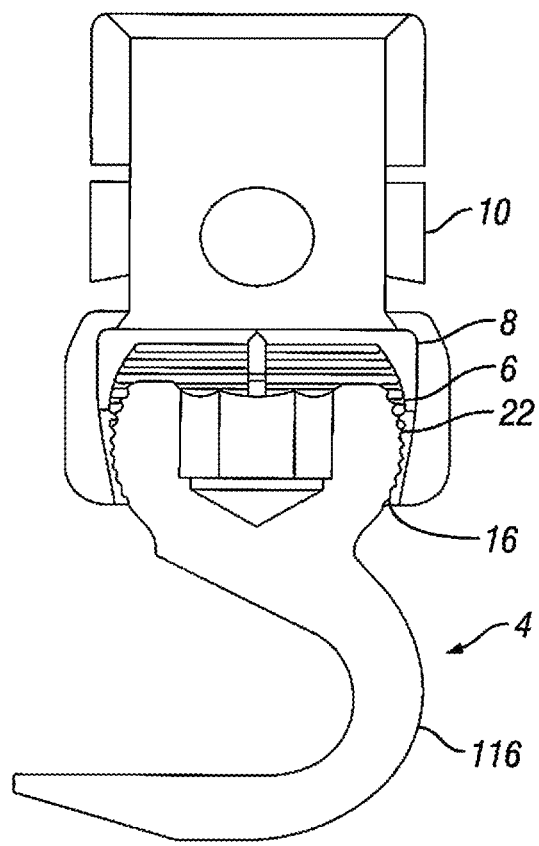
FIG. 23 illustrates an orthopedic fixation device comprising a bone hook in accordance embodiments of the present invention.

While the embodiments that are described and illustrated above generally illustrate a bone fastener 4 in shape of a screw having a head 16 and shaft 18 extending there from, it should be understood that other bone fasteners may also be used such as hooks and sacral blocks. Thus, the present invention may be used with a wide variety of bone fasteners in addition to a bone screw, as described above. For example, FIG. 23 illustrates an embodiment in which the bone fastener 14 includes a head 16 having an extension in the form of a hook 116 that extends from the head 16. In the illustrated embodiment, the head 16 is secured in the tulip element 10 by the clamp element 7 and the wedge element 8. As illustrated, the head 16 may have a roughened or textured surface 22 that improves engagement with the clamp element 7.

Figure 24:
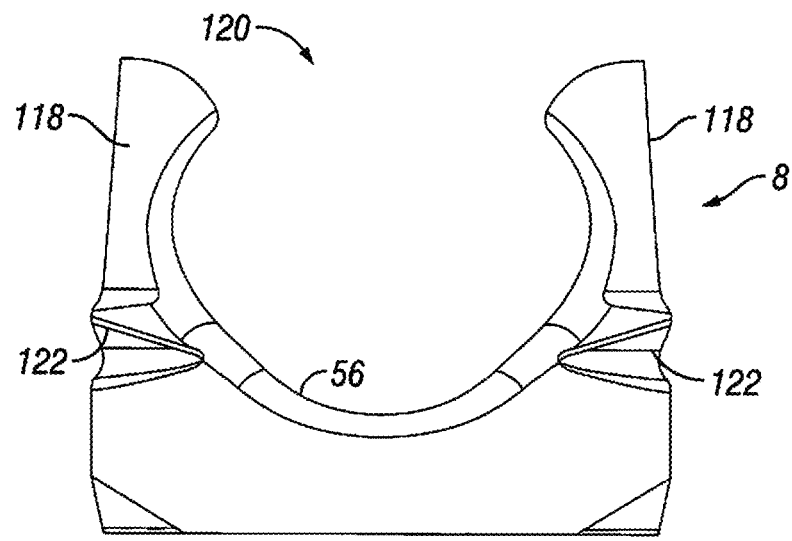
FIGS. 24-25 illustrate an alternative wedge element in accordance with embodiments of the present invention.
Figure 25:
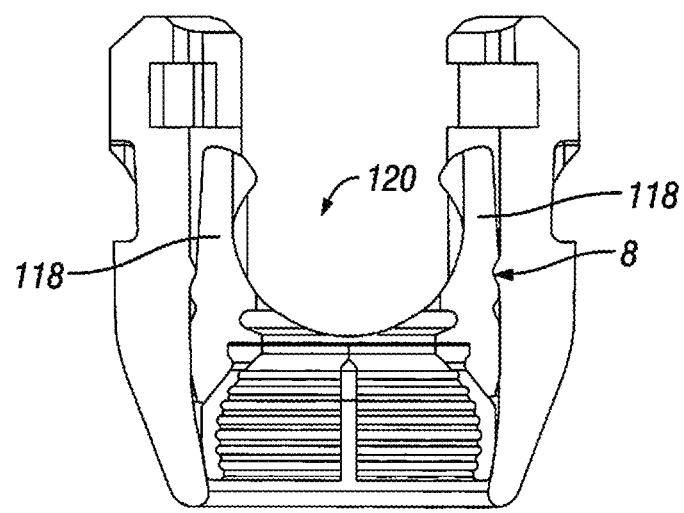

FIGS. 24 and 25 illustrate a wedge element 8 having an optional rod retention feature, in accordance with embodiments of the present invention. In some embodiments, the rod retention feature of the wedge element 8 may be added to enhance retainment of the rod 14 (e.g., FIG. 1) in a surgical procedure. In the illustrated embodiment, the rod retention feature is in the form of seat extensions 118 that will cradle the rod 14 to retain it in the wedge element 8. As illustrated, the wedge element 8 comprises an upper surface 56 defining a seat for receiving the rod 14. The wedge element 8 further may comprise seat extensions 118 for retaining the rod in the wedge element 8. In one embodiment, the seat extensions 118 may be configured to flex when a rod 14 is pushed down through opening 122 at the top of the seat extensions 118. When pressed down, the rod 14 may engage the ends of the seat extensions 118 causing the seat extensions 118 to flex outward increasing the size of the opening so that the rod 14 can be moved downwards to rest on the upper surface 56 of the wedge element 8. In other words, the rod 14 may be snapped past the seat extensions 118 in accordance with some embodiments. In the illustrated embodiment, the wedge element 8 further includes notches 122 to facilitate flexing of the seat extensions 118.

While the embodiments that are described and illustrated above generally illustrate a tulip element 10 in the general shape of a "U" for coupling the rod 14 to the bone fastener 4, it should be understood that any of a variety of different coupling elements may be used in accordance with embodiments of the present invention. For example, the coupling element may be open (e.g., tulip element 10 on FIG. 1) or closed. In some embodiments, the rod 14 may be top loaded into an open coupling element. In other embodiments, the rod 14 may be side loaded, for example, into a closed coupling element. In some embodiments, the coupling element may be an open, closed, or offset iliac connector. In yet other embodiments, the coupling element may be a posted screw connector. In addition, the coupling element may be configured to move polyaxially, monoaxially, or uni-planar with respect to the bone fastener 4 prior to locking of the coupling element onto the bone fastener 4.

Figure 26:
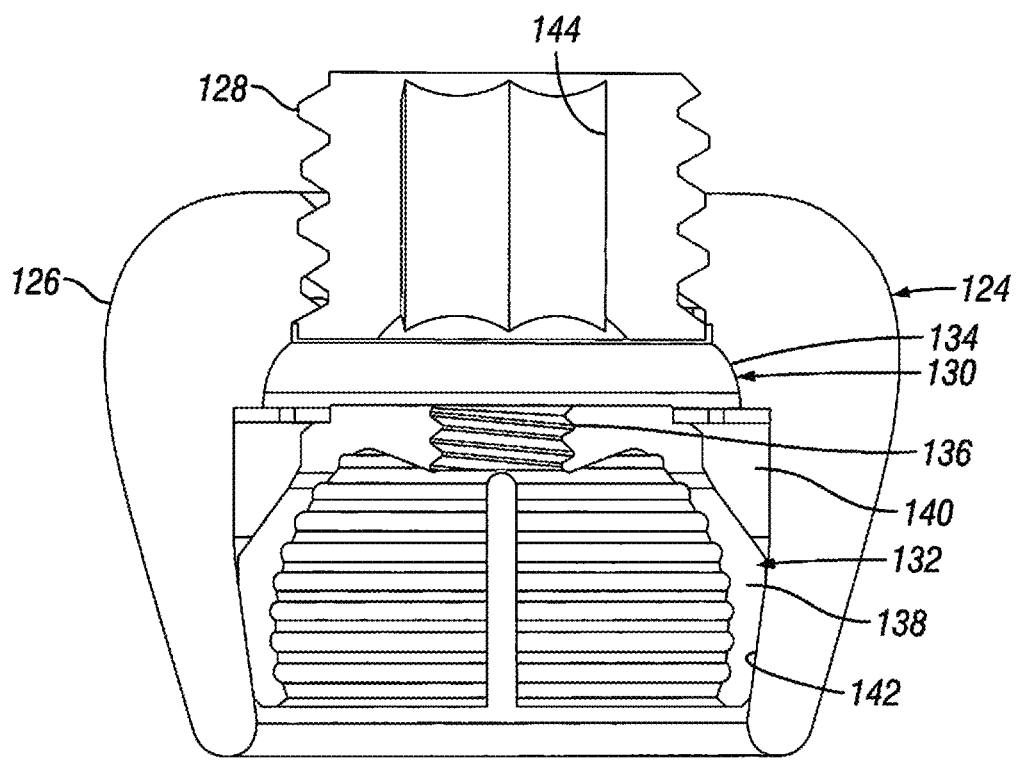
FIG. 26 illustrates an offset iliac connector in accordance with embodiments of the present invention.

FIG. 26 illustrates a coupling element in accordance with alternative embodiments of the present invention. In the illustrated embodiment, the coupling element is an offset iliac connector 124. The offset iliac connector 124 should allow, for example, iliac screw placement prior to selection of coupling element type. The design of the offset iliac connector 124 should also allow, for example, removal of the iliac connector 124 using a specialized instrument (not illustrated) to change the coupling element type in situ. As illustrated, the offset iliac connector 124 includes an offset housing 126, a set screw 128, a spring washer 130, and a locking clamp assembly 132. In accordance with embodiments of the present invention, the set screw 128 can be installed through the bottom of the offset housing 126 and rotated (e.g., counter clockwise) until tight. After installation of the set screw 128, the spring washer 130 may then be inserted upwardly through the bottom of the offset housing 126. In the illustrated embodiment, the spring washer 130 has a washer portion 134 and a spring portion 136 that extends down from the washer portion 134. The locking clamp assembly 132 may then be inserted upwardly through the bottom of the offset housing 126 and snapped into a place, in a manner similar to the previously described embodiments. In the illustrated embodiment, the locking clamp assembly 132 includes a wedge element 138 and a clamp element 140. To engage the offset connector with a head 16 of a bone fastener 4 (e.g., FIG. 1), the offset connector can be pushed down onto the head 16. The head 16 of the bone fastener 4 should be pushed upward into the locking clamp assembly 132. The bone fastener 4 should push the locking clamp assembly 132 upward into the spring portion 136 of the spring washer 130 until sufficient clearance is achieved between the locking clamp assembly 132 and the offset housing 126 for the bone fastener 4 to snap into the locking clamp assembly 132. The spring washer 130 should then provide downward force onto the locking clamp assembly 132 such that the interior wedge surface 142 of the offset housing 126 applies pressure to the locking clamp assembly 132 forcing the clamp element 138 to clamp onto the head 16 of the bone fastener 4. In some embodiments, a specialized instrument (not illustrate) can be threaded through the polygonal recess 144 (e.g., a hexagonal recess) in the set screw 128 and into the locking clamp assembly 132. The threading of the instrument should provide sufficient clearance with the offset housing 126 for removal of the offset iliac connector 124 from the bone fastener 4 without removal of the bone fastener 4 from the bone.

As previously illustrated and described with respect to FIG. 1, the tulip element 10 may include a threaded portion 72. FIGS. 27-29 illustrate the threaded portion 72 of the tulip element 10 in more detail. As illustrated, the tulip element 10 includes a body 65 and arms 66. As best seen in FIG. 28, the arms 66 each include an interior surface 70 having a threaded portion 72. In accordance with present embodiments, a bone fastener 4 can be secured to the tulip element 10. As illustrated, a tool 144, which may be, for example, a screw-driving tool, can be placed through the bore 62 in the tulip element 10 and into engagement with the tulip element 10 and the bone fastener 4. In the illustrated embodiment, the tool 144 includes a threaded portion 146 that engages the threaded portion 72 of the tulip element 10. The tool 144 further includes an engagement end 148 below the threaded portion 72 that engages with the polygonal recess 24 (e.g., hexagonal) in the head 16 of the bone fastener 4. In this manner, a rigid connection may be formed between the bone fastener 4 and the tool 144.

Figure 30:
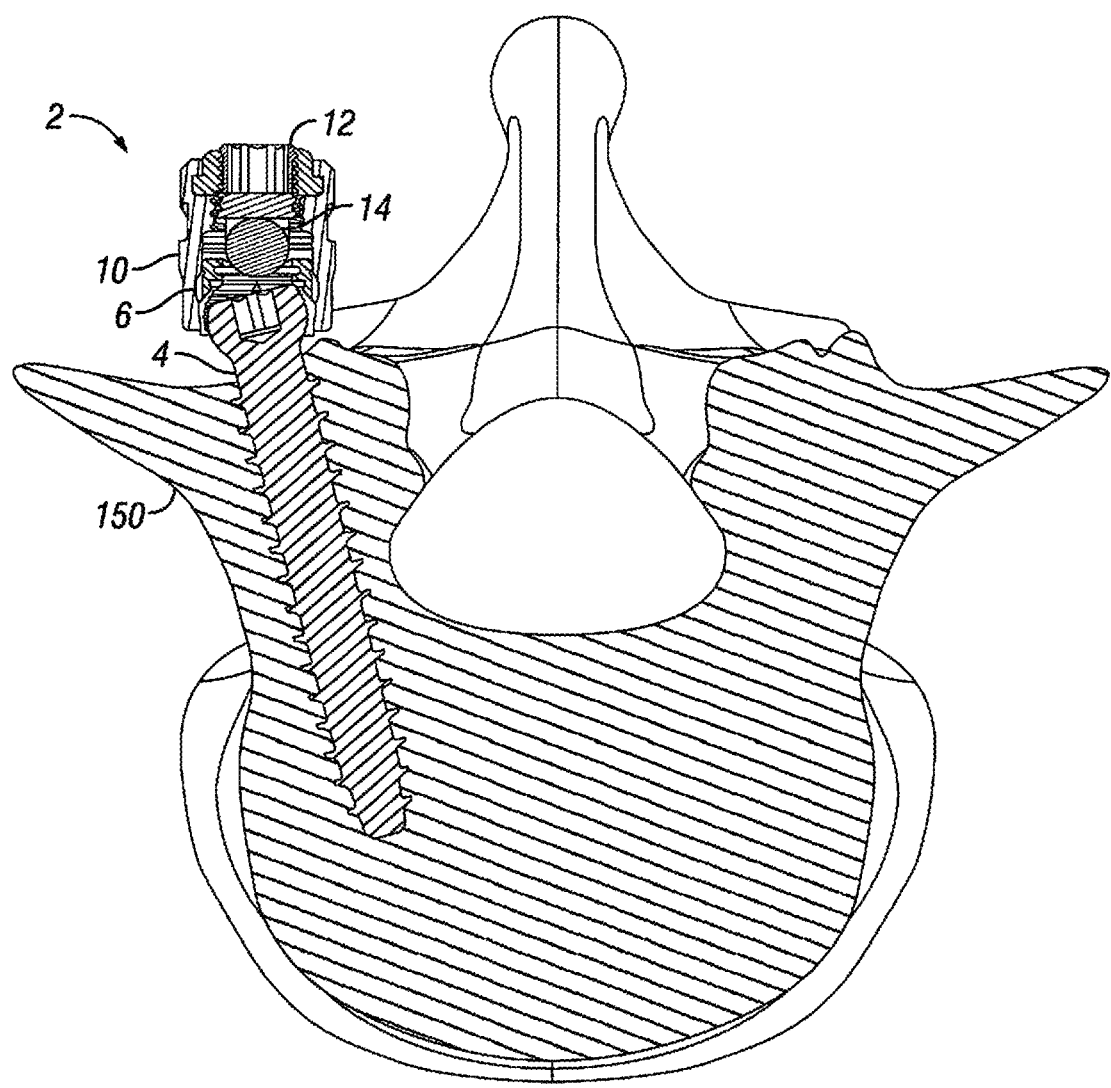
FIG. 30 illustrates a cross-sectional view of a vertebra having an orthopedic fixation device installed therein in accordance with embodiment of the present invention.

FIG. 30 illustrates installation of the orthopedic fixation device 2 in a vertebra 150 in accordance with embodiments of the present invention. As illustrated, the bone fastener 4 may be implanted into the vertebra 150. The bone fastener 4 may then be secured to the tulip element 10 using, for example, the locking clamp assembly 6. The tulip element 10 can then be moved and rotated into a desired position with respect to the bone fastener 4 and then locked onto the bone fastener 4. In one embodiment, the tulip element 10 is fixed onto the bone fastener 4 contemporaneously with securing the rod 14 to the tulip element 10 with the locking cap assembly 12. In this manner, the rod 14 can be secured in a fixed position relative to the vertebra 150.

FIGS. 31-34 illustrate one or more alternative embodiments consistent with the present disclosure. FIGS. 31-34 show one or more embodiments where the coupling element may be moved in a polyaxial direction when disposed on a screw head but not locked in position. The screw head may be inserted and removed through the bottom of the coupling element via a bore.

Figure 31:
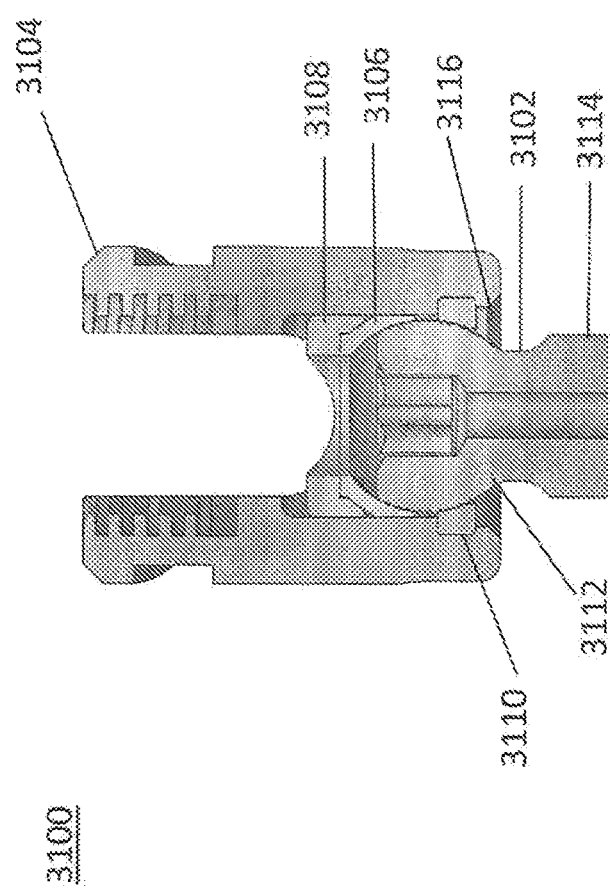
FIG. 31 illustrates a fixation device consistent with the present disclosure.

FIG. 31 illustrates a cross section of an orthopedic fixation device 3100 in accordance with an exemplary embodiment and comprises bone fastener 3102, a coupling element or tulip element 3104, clamp 3106, saddle 3108, and clip 3110. Bone faster 3102 may also include head 3112 and shaft 3114. Bone fastener 3102 may the same or similar to bone fasteners as previously described. Fixation device 3100 may provide functionality of locking tulip 3104 to the bone fastener 3102 by engaging a locking cap to tulip 3104. Such engagement, when a rod is disposed in tulip 3104, may provide a force upon saddle 3108 and clamp 3106 to press head 3112 against clip 3110. If the locking cap is removed, the force upon saddle 3108 and clamp 3106 is removed, tulip 3104 may be released from bone fastener 3102. In this embodiment, tulip 3104 with respect to bone fastener 3102 may become polyaxial once the force locking tulip 3104 to bone fastener 3102 is removed without any further need for additional steps or manipulation.

In FIG. 31, clamp 3106 may be spherical in shape and engage with saddle 3108 and head 3112. In an exemplary operation, saddle 3108 and clamp 3106 may be inserted into the bottom of tulip 3104. Saddle 3108 and clamp 3106 may be designed to be separate elements or may be designed to be coupled to one another. After saddle 3108 and clamp 3106 are inserted into a bore 3116 at the bottom of tulip 3104, head 3112 of bone fastener 3114 may be inserted into the bottom of the tulip 3104, followed by clip 3110. In an exemplary embodiment, clamp 3110 and head 3112 may move independently of each other to provide for polyaxial movement of the tulip with respect to the bone fastener. The polyaxial movement may be locked when a locking cap is provided on the top of tulip 3104 by engaging a rod disposed in tulip 3104 and the rod presses saddle 3108 downward. The downward movement of saddle 3108 presses head 3112 against clip 3110 and thereby locking tulip 3104 to bone fastener 3102.

Figure 32:
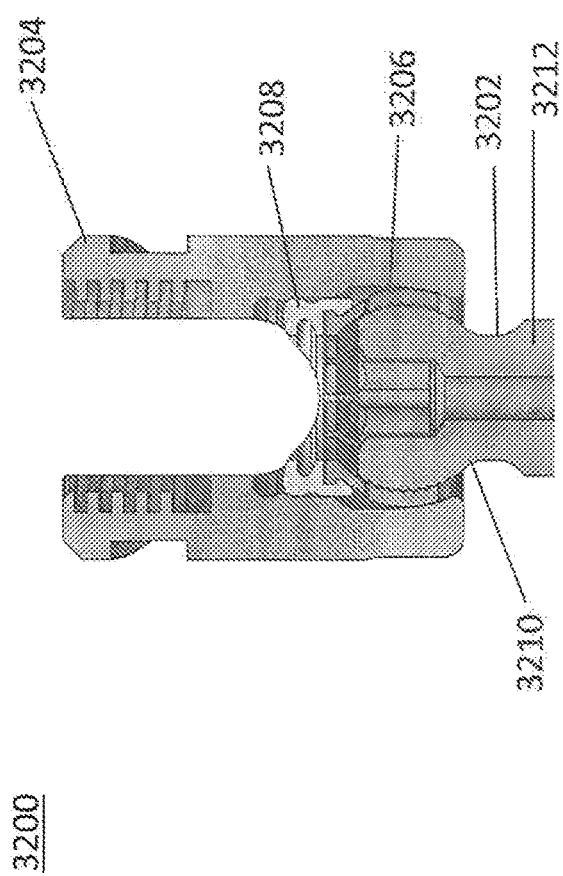
FIG. 32 illustrates a fixation device consistent with the present disclosure.

FIG. 32 shows another exemplary embodiment of the present disclosure. Fixation device 3200 may comprise bone fastener 3202, coupling element or tulip element 3204, clamp 3206, and saddle 3208. Bone faster 3202 may also include head 3210 and shaft 3212. Bone fastener 3202 may the same or similar to the bone fasteners already described herein. In contrast to fixation device 3100 of FIG. 31, fixation device 3200 of FIG. 32 does not include a clip. In operation, saddle 3208 and clamp 3206 are assembled together and inserted into the bottom of tulip 3204 to form a load position for receiving head 3210 of bone fastener 3202. Head 3210 is then inserted into the bottom of tulip 3204 to be received into clamp 3206. In an unlocked state, head 3210 may move independently from clamp 3206 to provide for polyaxial movement of the tulip with respect to the bone fastener. Tulip 3204 may be locked to head 3210 by inserting a locking cap into the top of tulip 3204 which presses a rod disposed in tulip 3204 against saddle 3208, which in turn presses against clamp 3206 and head 3210 towards the bottom of tulip 3204 thereby locking tulip 3204 to bone fastener 3202.

Figure 33:
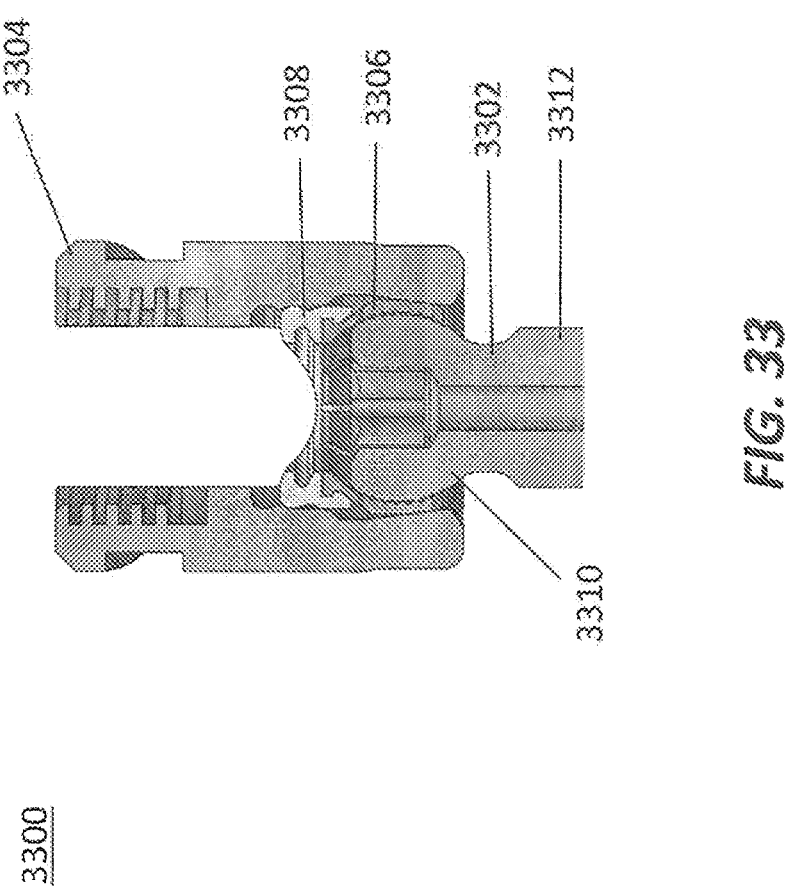
FIG. 33 illustrates a fixation device consistent with the present disclosure.

FIG. 33 shows another exemplary embodiment of the present disclosure. Fixation device 3300 may comprise bone fastener 3302, coupling element or tulip 3304, clamp 3306, and saddle 3308. Bone fastener 3302 may also include head 3310 and shaft 3312. Bone fastener 3302 may the same or similar to the bone fasteners already described herein. Tulip 3304 may be configured such that the portion of tulip 3304 receiving head 3310 may be tapered. In operation, saddle 3308 and clamp 3306 are assembled together and inserted into the bottom of tulip 3304 to form a load position for receiving head 3310 of bone fastener 3302. Head 3310 is then inserted into the bottom of tulip 3304 to be received into clamp 3306. In an unlocked state, head 3310 may move independently from clamp 3306 to provide for polyaxial movement of the tulip with respect to the bone fastener. Tulip 3304 may be locked to head 3310 by inserting a locking cap into the top of tulip 3304 which presses a rod disposed in tulip 3304 against saddle 3308, which in turn presses against clamp 3306 and head 3310 towards the bottom of tulip 3304 thereby locking tulip 3304 to head 3310. The bottom of tulip 3304 contains a tapered opening configured to engage head 3310 to lock fixation device 3300.

Figure 34:
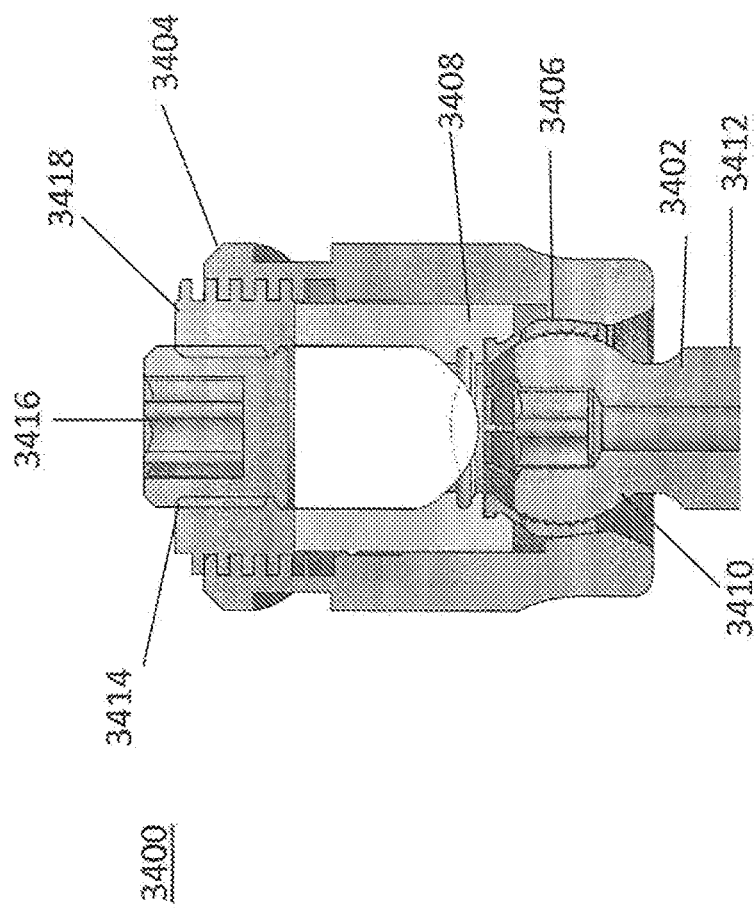
FIG. 34 illustrates a fixation device consistent with the present disclosure.

FIG. 34 shows another exemplary embodiment of the present disclosure. Fixation device 3400 may comprise bone fastener 3402, tulip 3404, clamp 3406, and saddle 3408. Bone fastener 3402 may also include head 3410 and shaft 3412. Bone fastener 3402 may the same or similar to the bone fasteners already described herein. Fixation device 3400 may also include a locking cap 3414 containing an inner screw 3416 and an outer screw 3418.

In operation, saddle 3408 and clamp 3406 are assembled together and inserted into the bottom of tulip 3404 to form a load position for receiving head 3410 of bone fastener 3412. Head 3410 is then inserted into the bottom of tulip 3404 to be received into clamp 3406. In an unlocked state, head 3410 may move independently from clamp 3406 to provide for polyaxial movement of the tulip with respect to the bone fastener. Tulip 3404 may be locked to head 3410 by turning outer screw 3418 which is configured to engage saddle 3408. This presses saddle 3408 downward, which in turn presses against clamp 3406 and head 3410 towards the bottom of tulip 3404 thereby locking tulip 3404 to head 3410. Inner screw 3416 may be twisted in order to engage a rod that would be disposed into an opening (for example, the U-shaped opening defined by tulip 3404 in FIG. 34). By twisting inner screw 3416, it engages the rod to prevent rod from moving.

Figure 35:
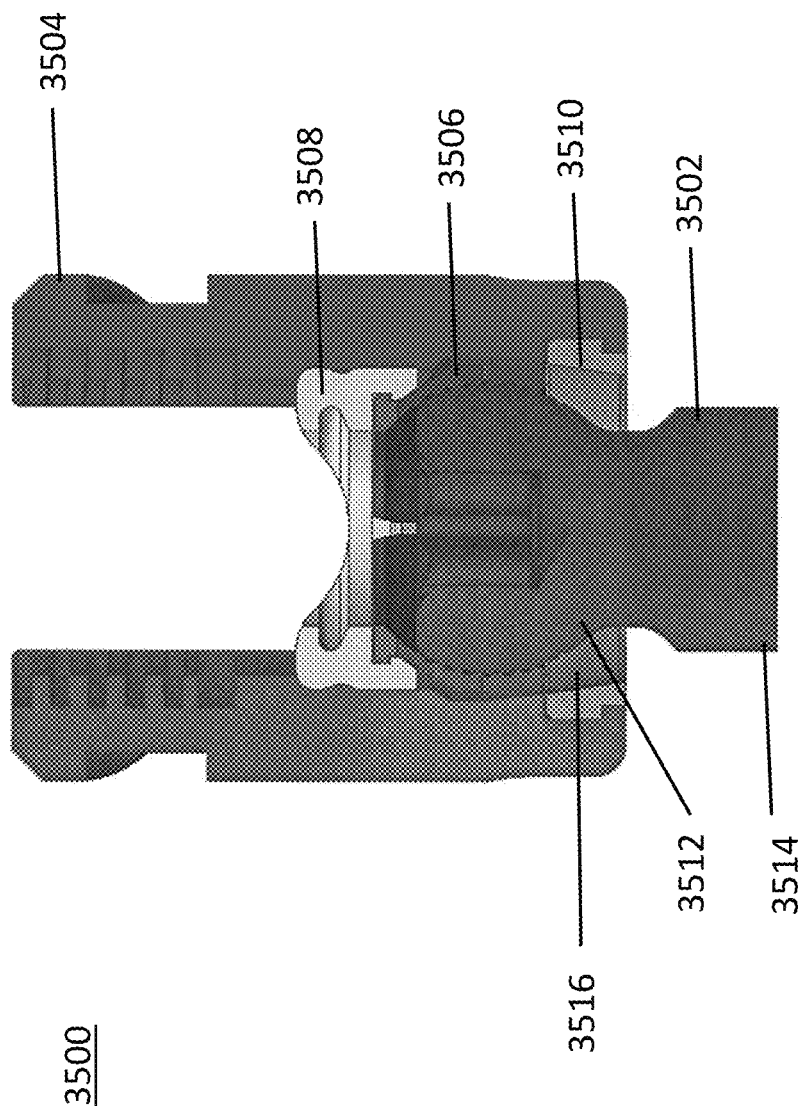
FIG. 35 illustrates a cross-sectional view of an exemplary fixation device consistent with the present disclosure.
Figure 36:
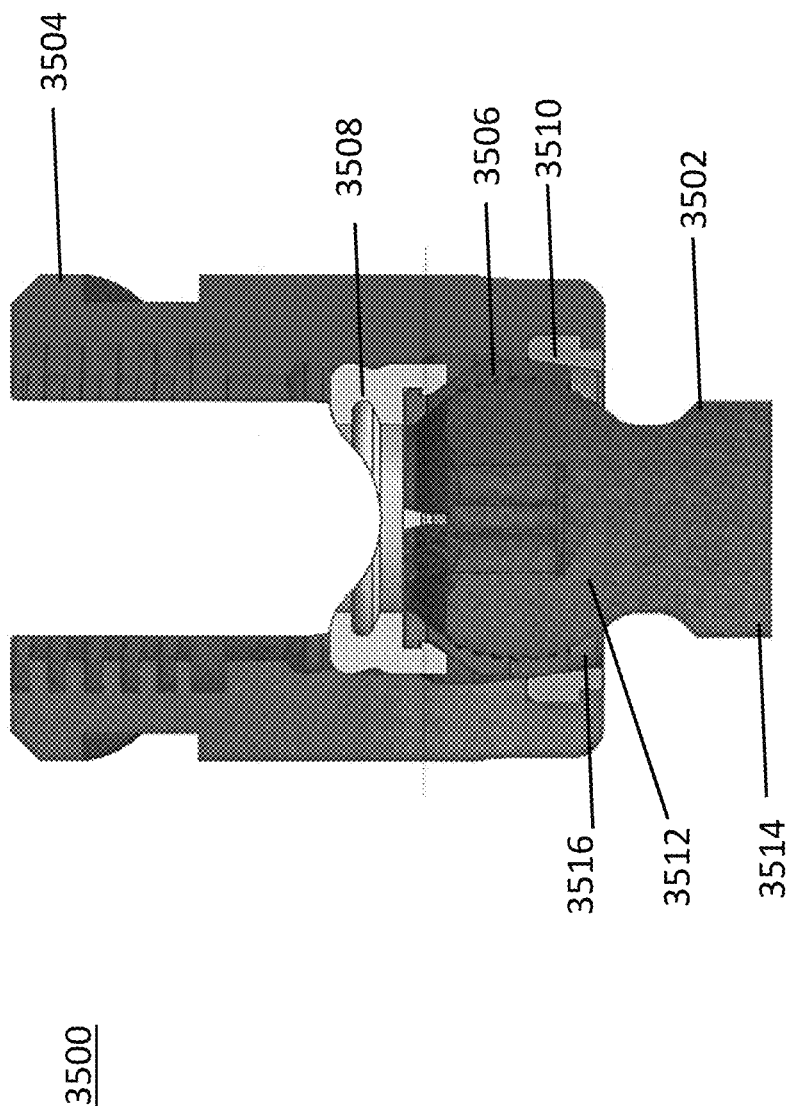
FIG. 36 illustrates a cross-sectional view of the fixation device of FIG. 35 consistent with the principles of the present disclosure.

FIGS. 35 and 36 illustrate another embodiment consistent with the principles of the present disclosure. Fixation device 3500 may comprise bone fastener 3502, tulip 3504, clamp 3506, saddle 3508, retention member 3510, and bore 3516. Bone fastener 3502 may also include head 3512 and shaft 3514. Bone fastener 3202 may the same or similar to the bone fasteners already described herein. As with embodiments previously described, the coupling element (e.g., tulip 3504 and associated components) may be moved in a polyaxial direction when disposed on a screw head but not locked in position. The screw head may be inserted and removed through the bottom of the coupling element via the bore.

In operation, fixation device 3500 functions in a way that is similar to previously described fixation devices. When assembled, screw head 3512 engages retention member 3510 and clamp 3506, which may be a one-piece clamp. Retention member 3510 allows for assembly of clamp 3506 and bone fastener 3502 from the bottom of tulip 3504 while maintaining a tapered locking mechanism. It may allow the taper angle to be varied to create a self-locking or self-releasing taper without increasing assembly difficulty.

Saddle 3508 and clamp 3506 may be first assembled into the bottom of tulip 3504, followed by retaining member 3510. A bone screw (fastener 3502) may then be assembled into clamp 3506, and saddle 3508 locked into place creating a polyaxial screw. Tulip 3504 may be configured in a manner such that a start of a locking taper is disposed at the bottom of tulip 3504 and when retention member 3510 is disposed in tulip 3504, retention member 3510 completes the taper. Retention member 3510 may be configured such that it does not retain bone screw until final tightening of a locking screw on a rod as previously described. This configuration before final tightening is shown in FIG. 35. FIG. 35 shows tulip in position to accept the bone screw (i.e., prior to locking saddle 3508 into place). As shown in FIG. 36, upon final tightening, saddle 3508 pushes clamp 3506 down the taper created by retaining member 3510 thereby locking the polyaxial motion of the bone screw (this figure shows tulip with saddle locked down meaning tulip will retain screw and screw will be polyaxial. It is not final tightened). Under this configuration by separating all or a portion of the taper from the tulip, fixation device 3500 provides a retention member that may allow for easy assembly from the bottom of the tulip regardless of clamp size and/or profile, while maintaining a tapered locking mechanism. The retention member may also allow the taper angle to be varied to create a self-locking or self-releasing taper without changing the tulip design and without increasing assembly difficulty.

Turning to FIGS. 37-42B, illustrated are various embodiments that may have the same or similar elements as previously described fixation devices, including for example, FIGS. 35-36. FIGS. 37-42B also illustrate various exemplary embodiments of providing a separated taper from the tulip in the form of a retention member that may be clipped or screwed into the bottom of the tulip.

Figure 37:
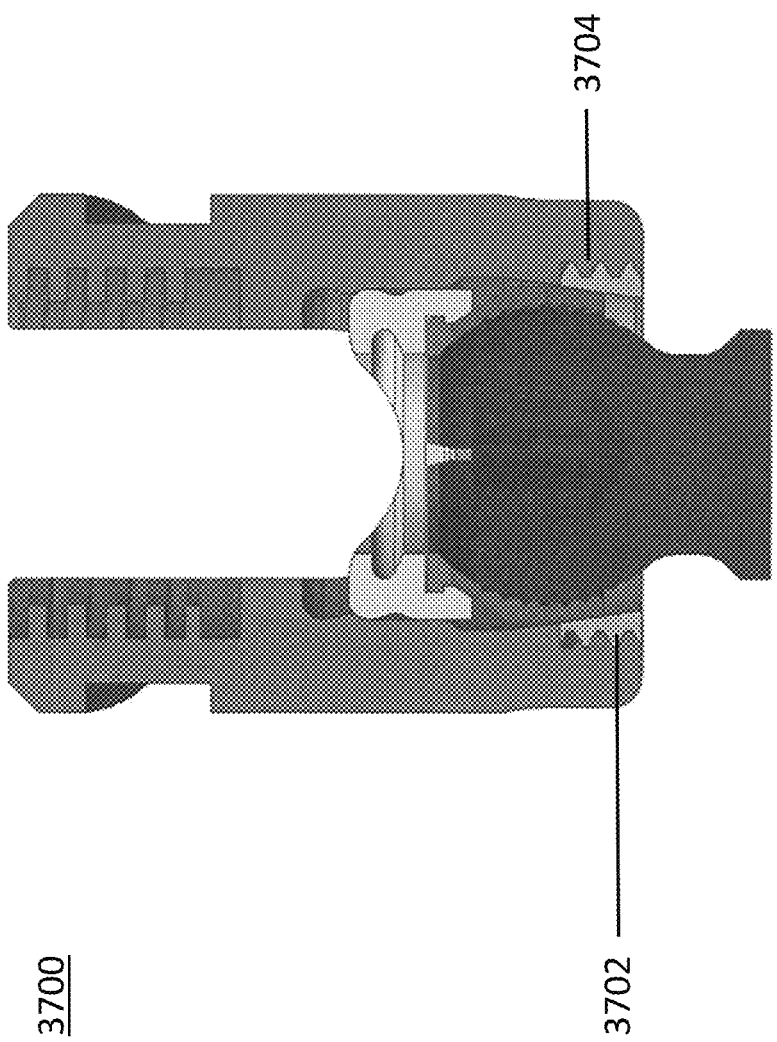
FIG. 37 illustrates a cross-sectional view of an exemplary fixation device consistent with the principles of the present disclosure.

FIG. 37 illustrates an exemplary fixation device 3700 having a retention member 3702. Retention member 3702 may be in the form of a threaded tapered ring that is screwed into the bottom of the tulip. For example, the tulip may contain threads 3704 that engage retention member 3702 to secure retention member 3702 to the tulip. As previously described, the saddle and one-piece clamp are assembled into the bottom of the tulip, followed by threading retention member 3702, in an exemplary form of a solid tapered ring, into the tulip. A bone screw can then be assembled into the clamp, and the saddle locked into place creating a polyaxial screw. The tulip contains the start of the locking taper, and the retention member 3702 as a threaded tapered ring, completes it. Retention member 3702 may be configured such that it does not retain the bone screw until final tightening. Upon final tightening, the clamp travels down the taper created by retention member 3102, and the polyaxial motion of the bone screw is locked.

Figure 38:
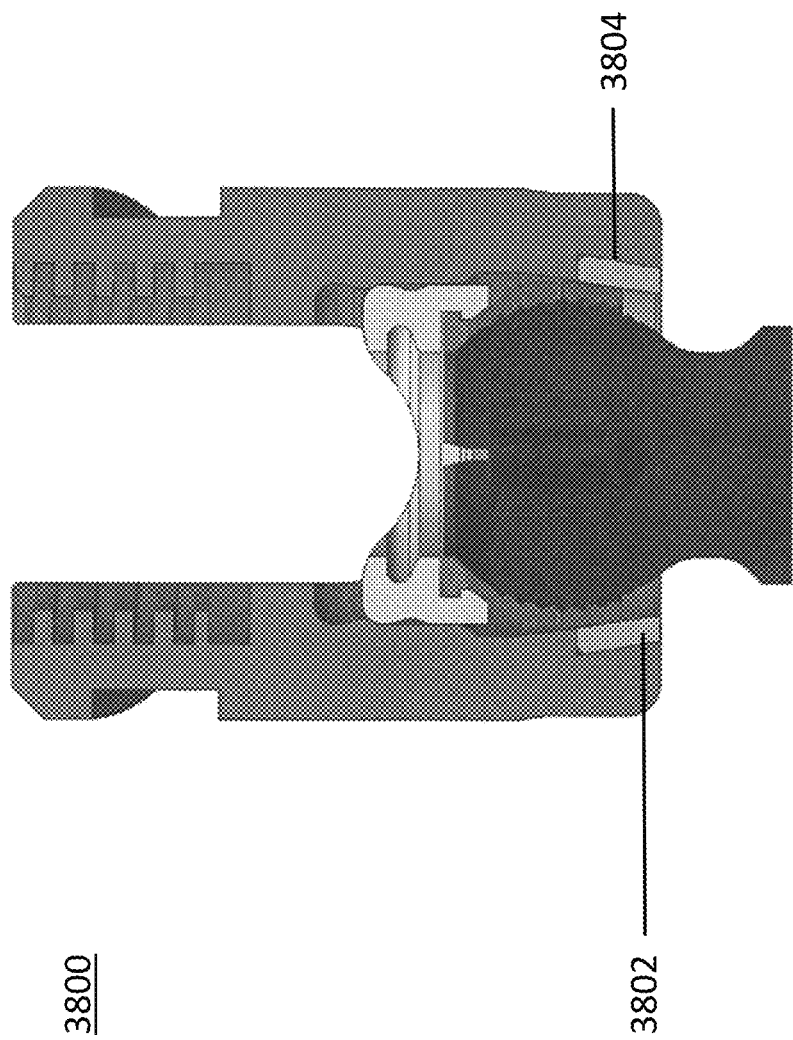
FIG. 38 illustrates a cross-sectional view of an exemplary fixation device consistent with the principles of the present disclosure.

FIG. 38 illustrates an exemplary fixation device 3800 having a retention member 3802 and a groove 3804. Retention member 3802 may be in the form of an angled clip that is secured to the tulip by engaging groove 3804. In operation, the saddle and one-piece clamp are assembled into the bottom of the tulip, followed by compressing an angled clip (for example, retention member 3802) and pressing it into the tulip. A bone screw can then be assembled into the clamp, and the saddle locked into place creating a polyaxial screw. Upon final tightening, the clamp travels down the taper created by the angled clip, and the polyaxial motion of the bone screw is locked.

Figure 39:
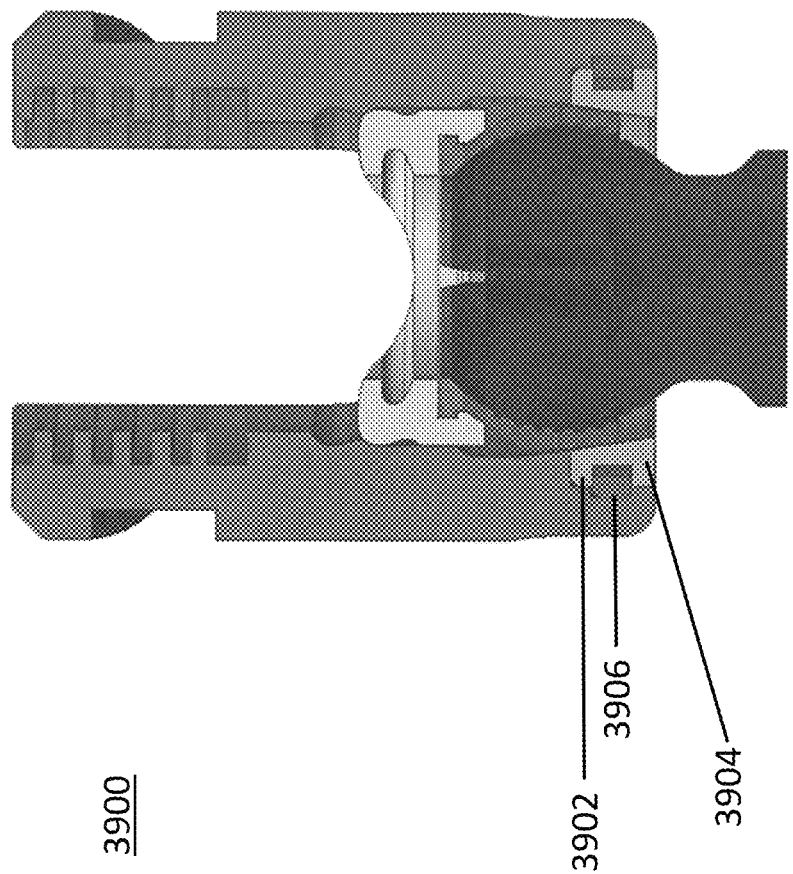
FIG. 39 illustrates a cross-sectional view of an exemplary fixation device consistent with the principles of the present disclosure.

FIG. 39 illustrates an exemplary fixation device 3900 having a retention member 3902. Retention member 3902 may be tapered ring 3904 with a clip 3906. In operation, the saddle and one-piece clamp are assembled into the bottom of the tulip. Clip 3906 may be assembled onto the tapered ring 3904 as shown in FIG. 39 and then pressing retention member 3902 into the tulip. A bone screw can then be assembled into the clamp, and the saddle locked into place creating a polyaxial screw. Upon final tightening, the clamp travels down the taper created by the retention member, and the polyaxial motion of the bone screw is locked.

Figure 40:
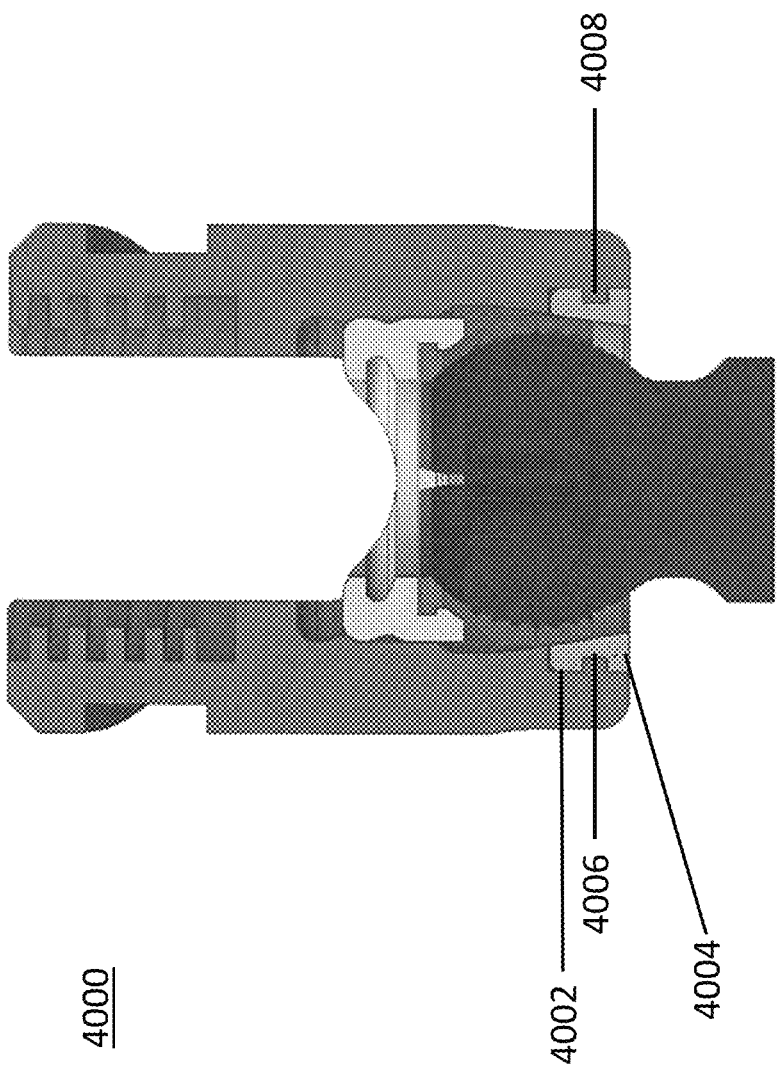
FIG. 40 illustrates a cross-sectional view of an exemplary fixation device consistent with the principles of the present disclosure.

FIG. 40 illustrates an exemplary fixation device 4000 having a retention member 4002. Retention member 4002 may be a tapered clip 4004 having a groove 4006. In operation, the saddle and one-piece clamp are assembled into the bottom of the tulip. Then, retention member 4002 is pressed into the tulip. In this example, groove 4006 may engage a portion of the tulip configured to receive 4006 such as a boss 4008. A bone screw can then be assembled into the clamp, and the saddle locked into place creating a polyaxial screw. Upon final tightening, the clamp travels down the taper created by the retention member, and the polyaxial motion of the bone screw is locked.

Figure 41:
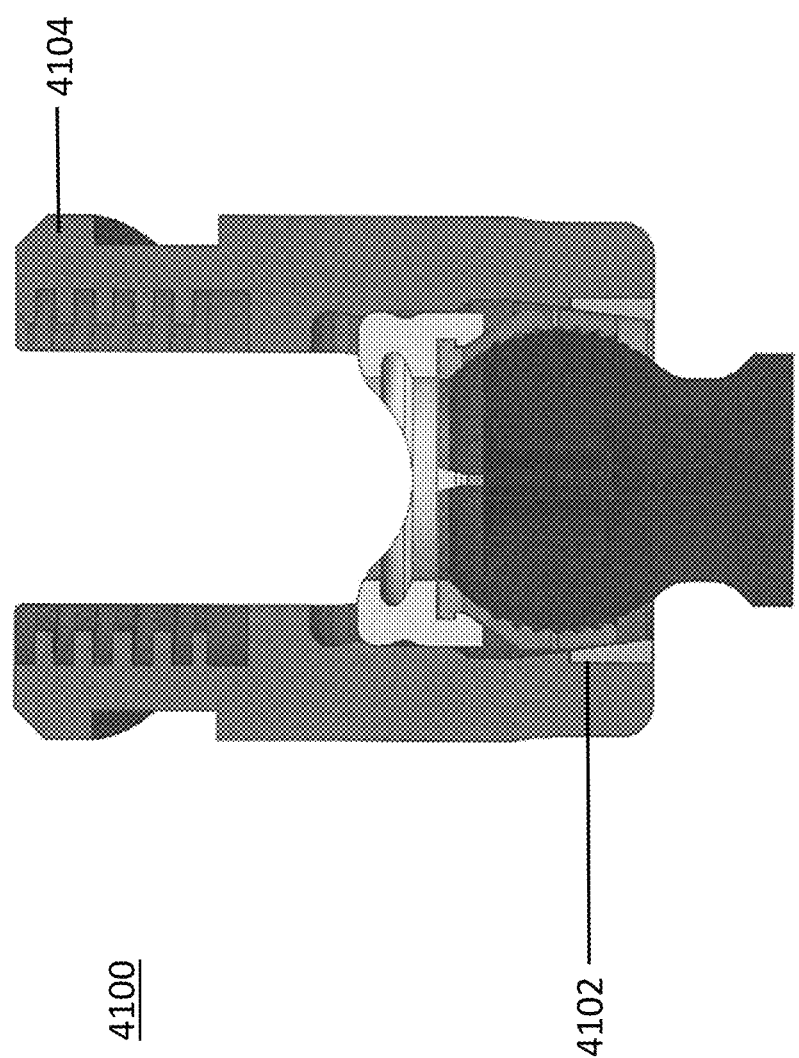
FIG. 41 illustrates a cross-sectional view of an exemplary fixation device consistent with the principles of the present disclosure.
Figure 42B:
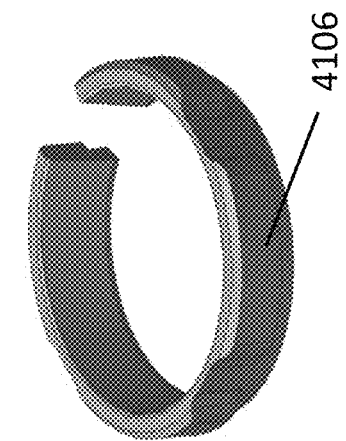
FIG. 42B illustrates a cross-sectional view of an exemplary retention member consistent with the principles of the present disclosure.
Figure 42A:
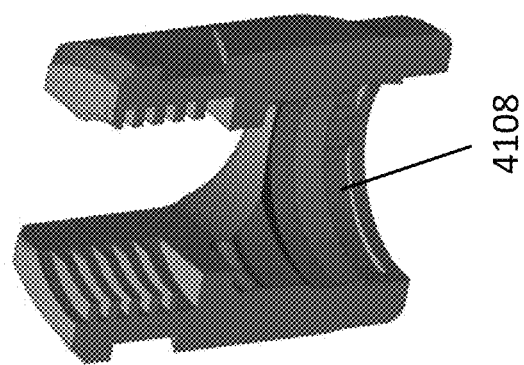
FIG. 42A illustrates a cross-sectional views of an exemplary coupling element consistent with the principles of the present disclosure.

FIG. 41 illustrates an exemplary fixation device 4100 having a retention member 4102 and tulip 4104. Retention member 4102 may be a tapered clip that has bosses 4106 that engage indentations 4108 in the bottom of tulip 4102 which are illustrated in FIGS. 42A-42B. In operation, the saddle and one-piece clamp are assembled into the bottom of the tulip. Then, retention member 4102 is pressed into the tulip. In this example, bosses 4106 may engage indentations 4108 to secure retention member 4102 to tulip 4104. A bone screw can then be assembled into the clamp, and the saddle locked into place creating a polyaxial screw. Upon final tightening, the clamp travels down the taper created by the retention member, and the polyaxial motion of the bone screw is locked.

Figure 44B:
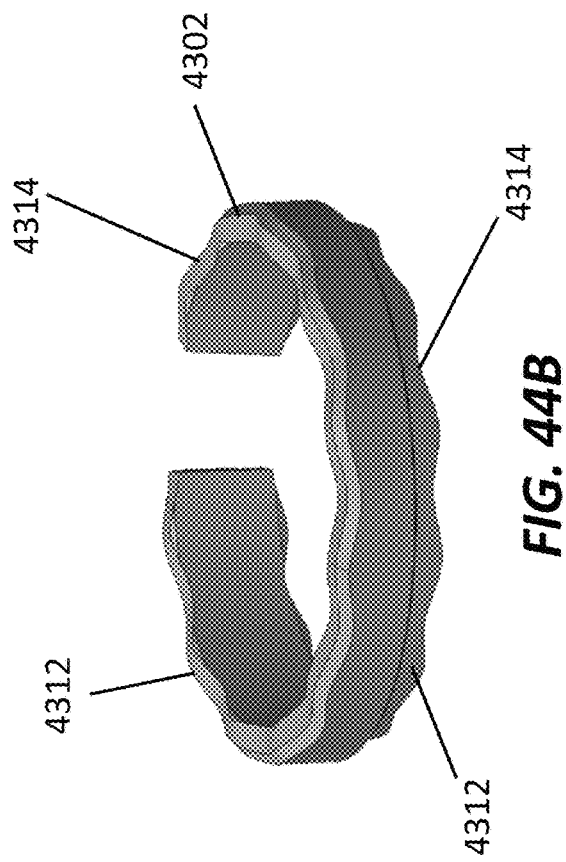
FIGS. 44A-44B illustrate the retention member of FIG. 43B consistent with the principles of the present disclosure.
Figure 44A:
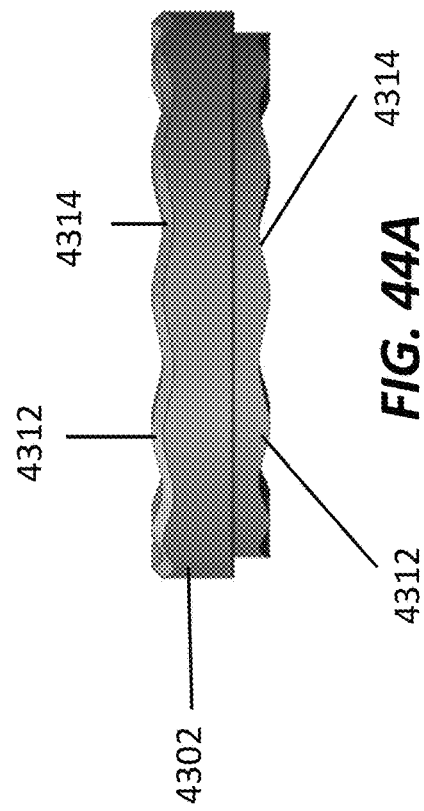

FIGS. 43A-43B illustrates a cross-sectional view of an exemplary retention member 4302 and tulip 4304. Tulip 4304 contains an indentation 4306 that may be configured to receive retention member 4302. Retention member 4302 is configured to be have an undulated top surface 4308 and an undulated bottom surface 4310. FIGS. 44A-44B illustrates retention member 4302 in greater detail. This creates one or more peaks 4312 and valleys 4314 on both surfaces which may create a non-planar configuration for retention member 4302. Indentation 4306 of tulip 4304 may also be configured with corresponding valleys and peaks designed to receive peaks 4312 and 4314. This may serve to limit rotation of retention member 4302 when engaged with tulip 4304. In operation, the saddle and one-piece clamp are assembled into the bottom of the tulip. Then, retention member 4302 is pressed into tulip 4304. In this example, retention member 4302 is received in indentation 4306. A bone screw can then be assembled into the clamp, and the saddle locked into place creating a polyaxial screw. Upon final tightening, the clamp travels down the taper created by the retention member, and the polyaxial motion of the bone screw is locked.

Figure 45B:
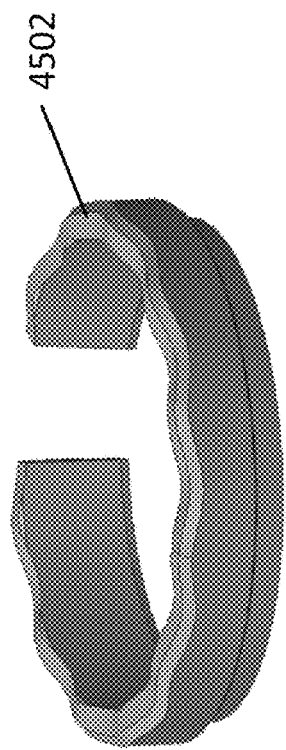
FIGS. 45A-45B illustrate an exemplary retention member consistent with the principles of the present disclosure.
Figure 45A:
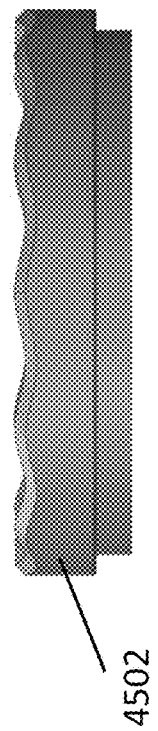
Figure 46B:
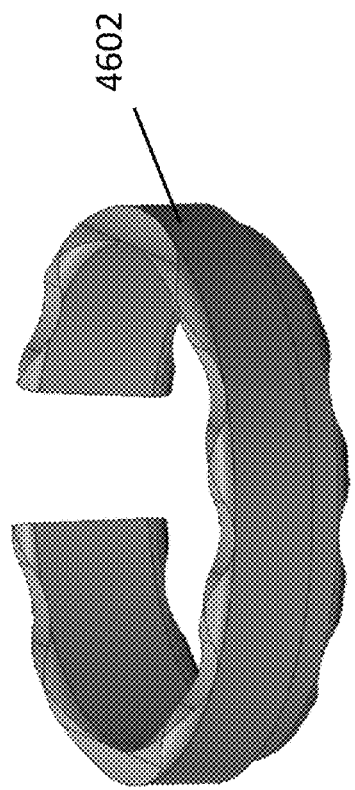
FIGS. 46A-46B illustrate an exemplary retention member consistent with the principles of the present disclosure.
Figure 46A:
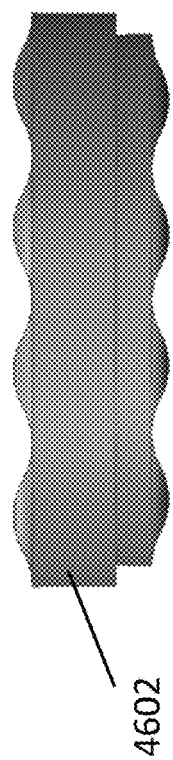
Figure 47B:
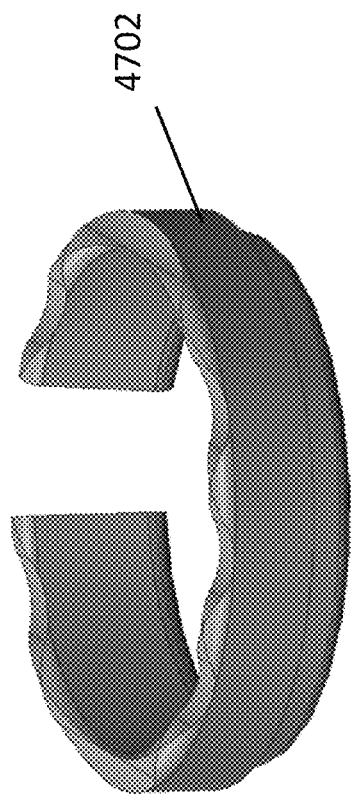
FIGS. 47A-47B illustrate an exemplary retention member consistent with the principles of the present disclosure.
Figure 47A:
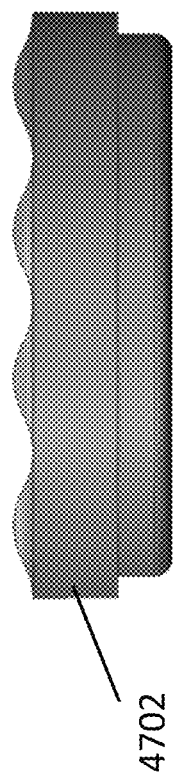

FIGS. 45A-47B illustrate other exemplary embodiments of the retention member. FIGS. 45A-45B show retention member 4502 with an undulated surface on the top and a straight surface on the bottom. FIGS. 46A-46B illustrate a retention member 4602 with undulated surfaces on the top and bottom surfaces. In this example, the undulated surface represents a straight cut as opposed to the radial cut shown in FIGS. 43B-44B. FIGS. 47A-47B illustrate retention member 4702 with a single undulated surface on the top and a straight surface on the bottom.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. An orthopedic fixation device comprising:
   a coupling element comprising a body having arms extending upward from the body, the arms defining a U-shaped channel configured to receive a rod, the body having a bore extending therethrough and an indentation within the body;
   a bone fastener having a head and an extension extending from the head, wherein the head is configured for loading into the coupling element through the bore;
   a clamp configured to receive the head of the bone fastener;
   a saddle configured to engage the clamp; and
   a retention member configured to engage the clamp, the retention member having a top surface and a bottom surface, wherein the retention member is disposed in the indentation within the coupling element, and the top surface or the bottom surface of the retention is non-planar.

2. The orthopedic fixation device of claim 1, wherein the top surface of the retention member is undulating and includes peaks and valleys.

3. The orthopedic fixation device of claim 1, wherein the bottom surface of the retention member is non-planar.

4. The orthopedic fixation device of claim 1, wherein the bottom surface of the retention member is undulating and includes peaks and valleys.

5. The orthopedic fixation device of claim 1, wherein the top surface of the retention member is non-planar and the bottom surface of the retention member is planar.

6. The orthopedic fixation device of claim 1, wherein the indentation includes an upper surface configured to contact at least a portion of the top surface of the retention member and a lower surface configured to contact at least a portion of the bottom surface of the retention member.

7. The orthopedic fixation device of claim 6, wherein the upper surface of the indentation is planar.

8. The orthopedic fixation device of claim 1, wherein the indentation is undulating with peaks and valleys corresponding to peaks and valleys of the retention member.

9. The orthopedic fixation device of claim 1 further comprising a locking cap assembly, wherein the locking cap assembly secures the rod to the coupling element.

10. The orthopedic fixation device of claim 1 wherein the bore of the coupling element is tapered.

11. An orthopedic fixation device comprising:
    a coupling element comprising a body having arms extending upward from the body, the arms defining a U-shaped channel configured to receive a rod, the body having a bore extending therethrough and an indentation within the body;
    a bone fastener having a head and an extension extending from the head, wherein the head is configured for loading into the coupling element through the bore;
    a clamp configured to receive the head of the bone fastener;
    a saddle configured to engage the clamp; and
    a retention member configured to engage the clamp, the retention member having a top surface and a bottom surface, wherein the retention member is disposed in the indentation within the coupling element, and the top surface of the retention is non-planar.

12. The orthopedic fixation device of claim 11, wherein the top surface of the retention member is undulating and includes peaks and valleys.

13. The orthopedic fixation device of claim 11, wherein the bottom surface of the retention member is non-planar.

14. The orthopedic fixation device of claim 11, wherein the bottom surface of the retention member is undulating and includes peaks and valleys.

15. The orthopedic fixation device of claim 11, wherein the bottom surface of the retention member is planar.

16. The orthopedic fixation device of claim 11, wherein the indentation includes an upper surface configured to contact at least a portion of the top surface of the retention member and a lower surface configured to contact at least a portion of the bottom surface of the retention member.

17. The orthopedic fixation device of claim 16, wherein the upper surface of the indentation is planar.

18. The orthopedic fixation device of claim 11, wherein the indentation is undulating with peaks and valleys corresponding to peaks and valleys of the retention member.

19. The orthopedic fixation device of claim 11 further comprising a locking cap assembly, wherein the locking cap assembly secures the rod to the coupling element.

20. The orthopedic fixation device of claim 11 wherein the bore of the coupling element is tapered.

* * * * *